(12) United States Patent
Hart et al.

(10) Patent No.: US 12,213,674 B2
(45) Date of Patent: Feb. 4, 2025

(54) DETERMINATION OF PREMATURE STAPLE EJECTION

(71) Applicant: Covidien LP, Mansfield, MA (US)

(72) Inventors: Alexander J. Hart, Tolland, CT (US); Charles R. Kollar, Washington, DC (US); James P. Delbo, North Haven, CT (US); Haley E. Strassner, Hamden, CT (US); Steven H. Joyce, Durham, CT (US)

(73) Assignee: Covidien LP, Mansfield, MA (US)

( * ) Notice: Subject to any disclaimer, the term of this patent is extended or adjusted under 35 U.S.C. 154(b) by 42 days.

(21) Appl. No.: 17/545,375

(22) Filed: Dec. 8, 2021

(65) Prior Publication Data

US 2023/0172609 A1     Jun. 8, 2023

(51) Int. Cl.
| A61B 17/072 | (2006.01) |
| A61B 17/115 | (2006.01) |
| A61B 17/00 | (2006.01) |
| A61B 17/11 | (2006.01) |

(52) U.S. Cl.
CPC . *A61B 17/1155* (2013.01); *A61B 2017/00017* (2013.01); *A61B 2017/1132* (2013.01)

(58) Field of Classification Search
CPC .................. A61B 17/068; A61B 2017/00017
See application file for complete search history.

(56) References Cited

U.S. PATENT DOCUMENTS

| 3,388,847 A | 6/1968 | Kasulin et al. |
| 3,552,626 A | 1/1971 | Astafiev et al. |
| 3,638,652 A | 2/1972 | Kelley |
| 3,771,526 A | 11/1973 | Rudie |
| 4,198,982 A | 4/1980 | Fortner et al. |
| 4,207,898 A | 6/1980 | Becht |
| 4,289,133 A | 9/1981 | Rothfuss |
| 4,304,236 A | 12/1981 | Conta et al. |
| 4,319,576 A | 3/1982 | Rothfuss |
| 4,350,160 A | 9/1982 | Kolesov et al. |

(Continued)

FOREIGN PATENT DOCUMENTS

| CA | 908529 A | 8/1972 |
| CA | 2805365 A1 | 8/2013 |

(Continued)

OTHER PUBLICATIONS

US 11,602,343 B2, 03/2023, Shelton, IV (withdrawn)*

(Continued)

*Primary Examiner* — Gloria R Weeks

(57) ABSTRACT

A surgical device includes a power source, a motor coupled to the power source, and a transmission assembly movable by the motor. The device also includes a reload coupled to the transmission assembly. The reload includes a plurality of staples ejectable by the transmission assembly. The device further includes a distance sensor configured to monitor operation of the transmission assembly and output distance data. The device additionally includes a controller configured to operate the motor to move the transmission assembly proximally from a distal position until a hard stop is reached, and determine whether the plurality of staples have been previously ejected based on the distance data.

17 Claims, 10 Drawing Sheets

(56) References Cited

U.S. PATENT DOCUMENTS

| | | |
|---|---|---|
| 4,351,466 A | 9/1982 | Noiles |
| 4,379,457 A | 4/1983 | Gravener et al. |
| 4,473,077 A | 9/1984 | Noiles et al. |
| 4,476,863 A | 10/1984 | Kanshin et al. |
| 4,485,817 A | 12/1984 | Swiggett |
| 4,488,523 A | 12/1984 | Shichman |
| 4,505,272 A | 3/1985 | Utyamyshev et al. |
| 4,505,414 A | 3/1985 | Filipi |
| 4,520,817 A | 6/1985 | Green |
| 4,550,870 A | 11/1985 | Krumme et al. |
| 4,573,468 A | 3/1986 | Conta et al. |
| 4,576,167 A | 3/1986 | Noiles |
| 4,592,354 A | 6/1986 | Rothfuss |
| 4,603,693 A | 8/1986 | Conta et al. |
| 4,606,343 A | 8/1986 | Conta et al. |
| 4,632,290 A | 12/1986 | Green et al. |
| 4,646,745 A | 3/1987 | Noiles |
| 4,665,917 A | 5/1987 | Clanton et al. |
| 4,667,673 A | 5/1987 | Li |
| 4,671,445 A | 6/1987 | Barker et al. |
| 4,700,703 A | 10/1987 | Resnick et al. |
| 4,703,887 A | 11/1987 | Clanton et al. |
| 4,708,141 A | 11/1987 | Inoue et al. |
| 4,717,063 A | 1/1988 | Ebihara |
| 4,752,024 A | 6/1988 | Green et al. |
| 4,754,909 A | 7/1988 | Barker et al. |
| 4,776,506 A | 10/1988 | Green |
| 4,817,847 A | 4/1989 | Redtenbacher et al. |
| 4,873,977 A | 10/1989 | Avant et al. |
| 4,893,662 A | 1/1990 | Gervasi |
| 4,903,697 A | 2/1990 | Resnick et al. |
| 4,907,591 A | 3/1990 | Vasconcellos et al. |
| 4,917,114 A | 4/1990 | Green et al. |
| 4,957,499 A | 9/1990 | Lipatov et al. |
| 4,962,877 A | 10/1990 | Hervas |
| 5,005,749 A | 4/1991 | Aranyi |
| 5,042,707 A | 8/1991 | Taheri |
| 5,047,039 A | 9/1991 | Avant et al. |
| 5,104,025 A | 4/1992 | Main et al. |
| 5,119,983 A | 6/1992 | Green et al. |
| 5,122,156 A | 6/1992 | Granger et al. |
| 5,139,513 A | 8/1992 | Segato |
| 5,158,222 A | 10/1992 | Green et al. |
| 5,188,638 A | 2/1993 | Tzakis |
| 5,193,731 A | 3/1993 | Aranyi |
| 5,197,648 A | 3/1993 | Gingold |
| 5,197,649 A | 3/1993 | Bessler et al. |
| 5,205,459 A | 4/1993 | Brinkerhoff et al. |
| 5,221,036 A | 6/1993 | Takase |
| 5,222,963 A | 6/1993 | Brinkerhoff et al. |
| 5,253,793 A | 10/1993 | Green et al. |
| 5,261,920 A | 11/1993 | Main et al. |
| 5,271,543 A | 12/1993 | Grant et al. |
| 5,271,544 A | 12/1993 | Fox et al. |
| 5,275,322 A | 1/1994 | Brinkerhoff et al. |
| 5,282,810 A | 2/1994 | Allen et al. |
| 5,285,944 A | 2/1994 | Green et al. |
| 5,285,945 A | 2/1994 | Brinkerhoff et al. |
| 5,292,053 A | 3/1994 | Bilotti et al. |
| 5,309,927 A | 5/1994 | Welch |
| 5,312,024 A | 5/1994 | Grant et al. |
| 5,314,435 A | 5/1994 | Green et al. |
| 5,314,436 A | 5/1994 | Wilk |
| 5,330,486 A | 7/1994 | Wilk |
| 5,333,773 A | 8/1994 | Main et al. |
| 5,344,059 A | 9/1994 | Green et al. |
| 5,346,115 A | 9/1994 | Perouse et al. |
| 5,348,259 A | 9/1994 | Blanco et al. |
| 5,350,104 A | 9/1994 | Main et al. |
| 5,355,897 A | 10/1994 | Pietrafitta et al. |
| 5,360,154 A | 11/1994 | Green |
| 5,368,215 A | 11/1994 | Green et al. |
| 5,392,979 A | 2/1995 | Green et al. |
| 5,395,030 A | 3/1995 | Kuramoto et al. |
| 5,403,333 A | 4/1995 | Kaster et al. |
| 5,404,870 A | 4/1995 | Brinkerhoff et al. |
| 5,411,508 A | 5/1995 | Bessler et al. |
| 5,425,738 A | 6/1995 | Gustafson et al. |
| 5,433,721 A | 7/1995 | Hooven et al. |
| 5,437,684 A | 8/1995 | Calabrese et al. |
| 5,439,156 A | 8/1995 | Grant et al. |
| 5,443,198 A | 8/1995 | Viola et al. |
| 5,447,514 A | 9/1995 | Gerry et al. |
| 5,454,825 A | 10/1995 | Van Leeuwen et al. |
| 5,464,144 A | 11/1995 | Guy et al. |
| 5,464,415 A | 11/1995 | Chen |
| 5,470,006 A | 11/1995 | Rodak |
| 5,474,223 A | 12/1995 | Viola et al. |
| 5,497,934 A | 3/1996 | Brady et al. |
| 5,503,635 A | 4/1996 | Sauer et al. |
| 5,522,534 A | 6/1996 | Viola et al. |
| 5,533,661 A | 7/1996 | Main et al. |
| 5,588,579 A | 12/1996 | Schnut et al. |
| 5,609,285 A | 3/1997 | Grant et al. |
| 5,626,591 A | 5/1997 | Kockerling et al. |
| 5,632,433 A | 5/1997 | Grant et al. |
| 5,639,008 A | 6/1997 | Gallagher et al. |
| 5,641,111 A | 6/1997 | Ahrens et al. |
| 5,658,300 A | 8/1997 | Bito et al. |
| 5,669,918 A | 9/1997 | Balazs et al. |
| 5,685,474 A | 11/1997 | Seeber |
| 5,709,335 A | 1/1998 | Heck |
| 5,715,987 A | 2/1998 | Kelley et al. |
| 5,718,360 A | 2/1998 | Green et al. |
| 5,720,755 A | 2/1998 | Dakov |
| 5,732,872 A | 3/1998 | Bolduc et al. |
| 5,749,896 A | 5/1998 | Cook |
| 5,758,814 A | 6/1998 | Gallagher et al. |
| 5,799,857 A | 9/1998 | Robertson et al. |
| 5,814,055 A | 9/1998 | Knodel et al. |
| 5,833,698 A | 11/1998 | Hinchliffe et al. |
| 5,836,503 A | 11/1998 | Ehrenfels et al. |
| 5,839,639 A | 11/1998 | Sauer et al. |
| 5,855,312 A | 1/1999 | Toledano |
| 5,860,581 A | 1/1999 | Robertson et al. |
| 5,868,760 A | 2/1999 | McGuckin, Jr. |
| 5,881,943 A | 3/1999 | Heck et al. |
| 5,915,616 A | 6/1999 | Viola et al. |
| 5,947,363 A | 9/1999 | Bolduc et al. |
| 5,951,576 A | 9/1999 | Wakabayashi |
| 5,957,363 A | 9/1999 | Heck |
| 5,993,468 A | 11/1999 | Rygaard |
| 6,024,748 A | 2/2000 | Manzo et al. |
| 6,050,472 A | 4/2000 | Shibata |
| 6,053,390 A | 4/2000 | Green et al. |
| 6,068,636 A | 5/2000 | Chen |
| 6,083,241 A | 7/2000 | Longo et al. |
| 6,102,271 A | 8/2000 | Longo et al. |
| 6,117,148 A | 9/2000 | Ravo et al. |
| 6,119,913 A | 9/2000 | Adams et al. |
| 6,126,058 A | 10/2000 | Adams et al. |
| 6,142,933 A | 11/2000 | Longo et al. |
| 6,149,667 A | 11/2000 | Hovland et al. |
| 6,176,413 B1 | 1/2001 | Heck et al. |
| 6,179,195 B1 | 1/2001 | Adams et al. |
| 6,193,129 B1 | 2/2001 | Bittner et al. |
| 6,203,553 B1 | 3/2001 | Robertson et al. |
| 6,209,773 B1 | 4/2001 | Bolduc et al. |
| 6,241,140 B1 | 6/2001 | Adams et al. |
| 6,253,984 B1 | 7/2001 | Heck et al. |
| 6,258,107 B1 | 7/2001 | Balazs et al. |
| 6,264,086 B1 | 7/2001 | McGuckin, Jr. |
| 6,269,997 B1 | 8/2001 | Balazs et al. |
| 6,273,897 B1 | 8/2001 | Dalessandro et al. |
| 6,279,809 B1 | 8/2001 | Nicolo |
| 6,302,311 B1 | 10/2001 | Adams et al. |
| 6,338,737 B1 | 1/2002 | Toledano |
| 6,343,731 B1 | 2/2002 | Adams et al. |
| 6,387,105 B1 | 5/2002 | Gifford, III et al. |
| 6,398,795 B1 | 6/2002 | McAlister et al. |
| 6,402,008 B1 | 6/2002 | Lucas |
| 6,439,446 B1 | 8/2002 | Perry et al. |
| 6,443,973 B1 | 9/2002 | Whitman |
| 6,450,390 B2 | 9/2002 | Heck et al. |

(56) References Cited

U.S. PATENT DOCUMENTS

| | | |
|---|---|---|
| 6,478,210 B2 | 11/2002 | Adams et al. |
| 6,488,197 B1 | 12/2002 | Whitman |
| 6,491,201 B1 | 12/2002 | Whitman |
| 6,494,877 B2 | 12/2002 | Odell et al. |
| 6,503,259 B2 | 1/2003 | Huxel et al. |
| 6,517,566 B1 | 2/2003 | Hovland et al. |
| 6,520,398 B2 | 2/2003 | Nicolo |
| 6,533,157 B1 | 3/2003 | Whitman |
| 6,551,334 B2 | 4/2003 | Blatter et al. |
| 6,578,751 B2 | 6/2003 | Hartwick |
| 6,585,144 B2 | 7/2003 | Adams et al. |
| 6,588,643 B2 | 7/2003 | Bolduc et al. |
| 6,592,596 B1 | 7/2003 | Geitz |
| 6,601,749 B2 | 8/2003 | Sullivan et al. |
| 6,605,078 B2 | 8/2003 | Adams |
| 6,605,098 B2 | 8/2003 | Nobis et al. |
| 6,626,921 B2 | 9/2003 | Blatter et al. |
| 6,629,630 B2 | 10/2003 | Adams |
| 6,631,837 B1 | 10/2003 | Heck |
| 6,632,227 B2 | 10/2003 | Adams |
| 6,632,237 B2 | 10/2003 | Ben-David et al. |
| 6,652,542 B2 | 11/2003 | Blatter et al. |
| 6,659,327 B2 | 12/2003 | Heck et al. |
| 6,676,671 B2 | 1/2004 | Robertson et al. |
| 6,681,979 B2 | 1/2004 | Whitman |
| 6,685,079 B2 | 2/2004 | Sharma et al. |
| 6,695,198 B2 | 2/2004 | Adams et al. |
| 6,695,199 B2 | 2/2004 | Whitman |
| 6,698,643 B2 | 3/2004 | Whitman |
| 6,716,222 B2 | 4/2004 | McAlister et al. |
| 6,716,233 B1 | 4/2004 | Whitman |
| 6,726,697 B2 | 4/2004 | Nicholas et al. |
| 6,742,692 B2 | 6/2004 | Hartwick |
| 6,743,244 B2 | 6/2004 | Blatter et al. |
| 6,763,993 B2 | 7/2004 | Bolduc et al. |
| 6,769,590 B2 | 8/2004 | Vresh et al. |
| 6,769,594 B2 | 8/2004 | Orban, III |
| 6,820,791 B2 | 11/2004 | Adams |
| 6,821,282 B2 | 11/2004 | Perry et al. |
| 6,827,246 B2 | 12/2004 | Sullivan et al. |
| 6,840,423 B2 | 1/2005 | Adams et al. |
| 6,843,403 B2 | 1/2005 | Whitman |
| 6,846,308 B2 | 1/2005 | Whitman et al. |
| 6,852,122 B2 | 2/2005 | Rush |
| 6,866,178 B2 | 3/2005 | Adams et al. |
| 6,872,214 B2 | 3/2005 | Sonnenschein et al. |
| 6,874,669 B2 | 4/2005 | Adams et al. |
| 6,884,250 B2 | 4/2005 | Monassevitch et al. |
| 6,905,504 B1 | 6/2005 | Vargas |
| 6,938,814 B2 | 9/2005 | Sharma et al. |
| 6,942,675 B1 | 9/2005 | Vargas |
| 6,945,444 B2 | 9/2005 | Gresham et al. |
| 6,953,138 B1 | 10/2005 | Dworak et al. |
| 6,957,758 B2 | 10/2005 | Aranyi |
| 6,959,851 B2 | 11/2005 | Heinrich |
| 6,978,922 B2 | 12/2005 | Bilotti et al. |
| 6,981,941 B2 | 1/2006 | Whitman et al. |
| 6,981,979 B2 | 1/2006 | Nicolo |
| 7,032,798 B2 | 4/2006 | Whitman et al. |
| 7,059,331 B2 | 6/2006 | Adams et al. |
| 7,059,510 B2 | 6/2006 | Orban, III |
| 7,077,856 B2 | 7/2006 | Whitman |
| 7,080,769 B2 | 7/2006 | Vresh et al. |
| 7,086,267 B2 | 8/2006 | Dworak et al. |
| 7,114,642 B2 | 10/2006 | Whitman |
| 7,118,528 B1 | 10/2006 | Piskun |
| 7,122,044 B2 | 10/2006 | Bolduc et al. |
| 7,128,748 B2 | 10/2006 | Mooradian et al. |
| 7,141,055 B2 | 11/2006 | Abrams et al. |
| 7,168,604 B2 | 1/2007 | Milliman et al. |
| 7,179,267 B2 | 2/2007 | Nolan et al. |
| 7,182,239 B1 | 2/2007 | Myers |
| 7,195,142 B2 | 3/2007 | Orban, III |
| 7,207,168 B2 | 4/2007 | Doepker et al. |
| 7,220,237 B2 | 5/2007 | Gannoe et al. |
| 7,234,624 B2 | 6/2007 | Gresham et al. |
| 7,235,089 B1 | 6/2007 | McGuckin, Jr. |
| RE39,841 E | 9/2007 | Bilotti et al. |
| 7,285,125 B2 | 10/2007 | Viola |
| 7,303,106 B2 | 12/2007 | Milliman et al. |
| 7,303,107 B2 | 12/2007 | Milliman et al. |
| 7,309,341 B2 | 12/2007 | Ortiz et al. |
| 7,322,994 B2 | 1/2008 | Nicholas et al. |
| 7,325,713 B2 | 2/2008 | Aranyi |
| 7,334,718 B2 | 2/2008 | McAlister et al. |
| 7,335,212 B2 | 2/2008 | Edoga et al. |
| 7,364,060 B2 | 4/2008 | Milliman |
| 7,398,908 B2 | 7/2008 | Holsten et al. |
| 7,399,305 B2 | 7/2008 | Csiky et al. |
| 7,401,721 B2 | 7/2008 | Holsten et al. |
| 7,401,722 B2 | 7/2008 | Hur |
| 7,407,075 B2 | 8/2008 | Holsten et al. |
| 7,410,086 B2 | 8/2008 | Ortiz et al. |
| 7,422,137 B2 | 9/2008 | Manzo |
| 7,422,138 B2 | 9/2008 | Bilotti et al. |
| 7,431,191 B2 | 10/2008 | Milliman |
| 7,438,718 B2 | 10/2008 | Milliman et al. |
| 7,455,676 B2 | 11/2008 | Holsten et al. |
| 7,455,682 B2 | 11/2008 | Viola |
| 7,481,347 B2 | 1/2009 | Roy |
| 7,494,038 B2 | 2/2009 | Milliman |
| 7,506,791 B2 | 3/2009 | Omaits et al. |
| 7,516,877 B2 | 4/2009 | Aranyi |
| 7,527,185 B2 | 5/2009 | Harari et al. |
| 7,537,602 B2 | 5/2009 | Whitman |
| 7,540,839 B2 | 6/2009 | Butler et al. |
| 7,546,939 B2 | 6/2009 | Adams et al. |
| 7,546,940 B2 | 6/2009 | Milliman et al. |
| 7,547,312 B2 | 6/2009 | Bauman et al. |
| 7,556,186 B2 | 7/2009 | Milliman |
| 7,559,451 B2 | 7/2009 | Sharma et al. |
| 7,585,306 B2 | 9/2009 | Abbott et al. |
| 7,588,174 B2 | 9/2009 | Holsten et al. |
| 7,600,663 B2 | 10/2009 | Green |
| 7,611,038 B2 | 11/2009 | Racenet et al. |
| 7,635,385 B2 | 12/2009 | Milliman et al. |
| 7,669,747 B2 | 3/2010 | Weisenburgh, II et al. |
| 7,686,201 B2 | 3/2010 | Csiky |
| 7,694,864 B2 | 4/2010 | Okada et al. |
| 7,699,204 B2 | 4/2010 | Viola |
| 7,708,181 B2 | 5/2010 | Cole et al. |
| 7,717,313 B2 | 5/2010 | Criscuolo et al. |
| 7,721,932 B2 | 5/2010 | Cole et al. |
| 7,726,539 B2 | 6/2010 | Holsten et al. |
| 7,743,958 B2 | 6/2010 | Orban, III |
| 7,744,627 B2 | 6/2010 | Orban, III et al. |
| 7,770,776 B2 | 8/2010 | Chen et al. |
| 7,771,440 B2 | 8/2010 | Ortiz et al. |
| 7,776,060 B2 | 8/2010 | Mooradian et al. |
| 7,793,813 B2 | 9/2010 | Bettuchi |
| 7,802,712 B2 | 9/2010 | Milliman et al. |
| 7,803,151 B2 * | 9/2010 | Whitman ............... A61B 90/98 |
| | | 702/158 |
| 7,823,592 B2 | 11/2010 | Bettuchi et al. |
| 7,837,079 B2 | 11/2010 | Holsten et al. |
| 7,837,080 B2 | 11/2010 | Schwemberger |
| 7,837,081 B2 | 11/2010 | Holsten et al. |
| 7,845,536 B2 | 12/2010 | Viola et al. |
| 7,845,538 B2 | 12/2010 | Whitman |
| 7,857,187 B2 | 12/2010 | Milliman |
| 7,886,951 B2 | 2/2011 | Hessler |
| 7,896,215 B2 | 3/2011 | Adams et al. |
| 7,900,806 B2 | 3/2011 | Chen et al. |
| 7,909,039 B2 | 3/2011 | Hur |
| 7,909,219 B2 | 3/2011 | Cole et al. |
| 7,909,222 B2 | 3/2011 | Cole et al. |
| 7,909,223 B2 | 3/2011 | Cole et al. |
| 7,913,892 B2 | 3/2011 | Cole et al. |
| 7,918,377 B2 | 4/2011 | Measamer et al. |
| 7,922,062 B2 | 4/2011 | Cole et al. |
| 7,922,743 B2 | 4/2011 | Heinrich et al. |
| 7,931,183 B2 | 4/2011 | Orban, III |
| 7,938,307 B2 | 5/2011 | Bettuchi |
| 7,942,302 B2 | 5/2011 | Roby et al. |

(56) References Cited

U.S. PATENT DOCUMENTS

| | | |
|---|---|---|
| 7,951,166 B2 | 5/2011 | Orban, III et al. |
| 7,959,050 B2 | 6/2011 | Smith et al. |
| 7,967,181 B2 | 6/2011 | Viola et al. |
| 7,975,895 B2 | 7/2011 | Milliman |
| 8,002,795 B2 | 8/2011 | Beetel |
| 8,006,701 B2 | 8/2011 | Bilotti et al. |
| 8,006,889 B2 | 8/2011 | Adams et al. |
| 8,011,551 B2 | 9/2011 | Marczyk et al. |
| 8,011,554 B2 | 9/2011 | Milliman |
| 8,016,177 B2 | 9/2011 | Bettuchi et al. |
| 8,016,858 B2 | 9/2011 | Whitman |
| 8,020,741 B2 | 9/2011 | Cole et al. |
| 8,025,199 B2 | 9/2011 | Whitman et al. |
| 8,028,885 B2 | 10/2011 | Smith et al. |
| 8,038,046 B2 | 10/2011 | Smith et al. |
| 8,043,207 B2 | 10/2011 | Adams |
| 8,066,167 B2 | 11/2011 | Measamer et al. |
| 8,066,169 B2 | 11/2011 | Viola |
| 8,070,035 B2 | 12/2011 | Holsten et al. |
| 8,070,037 B2 | 12/2011 | Csiky |
| 8,096,458 B2 | 1/2012 | Hessler |
| 8,109,426 B2 | 2/2012 | Milliman et al. |
| 8,109,427 B2 | 2/2012 | Orban, III |
| 8,113,405 B2 | 2/2012 | Milliman |
| 8,113,406 B2 | 2/2012 | Holsten et al. |
| 8,113,407 B2 | 2/2012 | Holsten et al. |
| 8,123,103 B2 | 2/2012 | Milliman |
| 8,128,645 B2 | 3/2012 | Sonnenschein et al. |
| 8,132,703 B2 | 3/2012 | Milliman et al. |
| 8,136,712 B2 | 3/2012 | Zingman |
| 8,146,790 B2 | 4/2012 | Milliman |
| 8,146,791 B2 | 4/2012 | Bettuchi et al. |
| 8,181,838 B2 | 5/2012 | Milliman et al. |
| 8,192,460 B2 | 6/2012 | Orban, III et al. |
| 8,201,720 B2 | 6/2012 | Hessler |
| 8,203,782 B2 | 6/2012 | Brueck et al. |
| 8,211,130 B2 | 7/2012 | Viola |
| 8,225,799 B2 | 7/2012 | Bettuchi |
| 8,225,981 B2 | 7/2012 | Criscuolo et al. |
| 8,231,041 B2 | 7/2012 | Marczyk et al. |
| 8,231,042 B2 | 7/2012 | Hessler et al. |
| 8,257,391 B2 | 9/2012 | Orban, III et al. |
| 8,267,301 B2 | 9/2012 | Milliman et al. |
| 8,272,552 B2 | 9/2012 | Holsten et al. |
| 8,276,802 B2 | 10/2012 | Kostrzewski |
| 8,281,975 B2 | 10/2012 | Criscuolo et al. |
| 8,286,845 B2 | 10/2012 | Perry et al. |
| 8,308,045 B2 | 11/2012 | Bettuchi et al. |
| 8,312,885 B2 | 11/2012 | Bettuchi et al. |
| 8,313,014 B2 | 11/2012 | Bettuchi |
| 8,317,073 B2 | 11/2012 | Milliman et al. |
| 8,317,074 B2 | 11/2012 | Ortiz et al. |
| 8,322,590 B2 | 12/2012 | Patel et al. |
| 8,328,060 B2 | 12/2012 | Jankowski et al. |
| 8,328,062 B2 | 12/2012 | Viola |
| 8,328,063 B2 | 12/2012 | Milliman et al. |
| 8,343,185 B2 | 1/2013 | Milliman et al. |
| 8,353,438 B2 | 1/2013 | Baxter, III et al. |
| 8,353,439 B2 | 1/2013 | Baxter, III et al. |
| 8,353,930 B2 | 1/2013 | Heinrich et al. |
| 8,360,295 B2 | 1/2013 | Milliman et al. |
| 8,365,974 B2 | 2/2013 | Milliman |
| 8,403,942 B2 | 3/2013 | Milliman et al. |
| 8,408,441 B2 | 4/2013 | Wenchell et al. |
| 8,413,870 B2 | 4/2013 | Pastorelli et al. |
| 8,413,872 B2 | 4/2013 | Patel |
| 8,418,905 B2 | 4/2013 | Milliman |
| 8,418,909 B2 | 4/2013 | Kostrzewski |
| 8,424,535 B2 | 4/2013 | Hessler et al. |
| 8,424,741 B2 | 4/2013 | McGuckin, Jr. et al. |
| 8,430,291 B2 | 4/2013 | Heinrich et al. |
| 8,430,292 B2 | 4/2013 | Patel et al. |
| 8,453,910 B2 | 6/2013 | Bettuchi et al. |
| 8,453,911 B2 | 6/2013 | Milliman et al. |
| 8,479,968 B2 | 7/2013 | Hodgkinson et al. |
| 8,485,414 B2 | 7/2013 | Criscuolo et al. |
| 8,490,853 B2 | 7/2013 | Criscuolo et al. |
| 8,511,533 B2 | 8/2013 | Viola et al. |
| 8,551,138 B2 | 10/2013 | Orban, III et al. |
| 8,567,655 B2 | 10/2013 | Nalagatla et al. |
| 8,579,178 B2 | 11/2013 | Holsten et al. |
| 8,590,763 B2 | 11/2013 | Milliman |
| 8,590,764 B2 | 11/2013 | Hartwick et al. |
| 8,608,047 B2 | 12/2013 | Holsten et al. |
| 8,616,428 B2 | 12/2013 | Milliman et al. |
| 8,616,429 B2 | 12/2013 | Viola |
| 8,622,275 B2 | 1/2014 | Baxter, III et al. |
| 8,627,995 B2 | 1/2014 | Smith et al. |
| 8,631,993 B2 | 1/2014 | Kostrzewski |
| 8,636,187 B2 | 1/2014 | Hueil et al. |
| 8,640,940 B2 | 2/2014 | Ohdaira |
| 8,646,674 B2 | 2/2014 | Schulte et al. |
| 8,662,370 B2 | 3/2014 | Takei |
| 8,663,258 B2 | 3/2014 | Bettuchi et al. |
| 8,672,207 B2 | 3/2014 | Shelton, IV et al. |
| 8,672,931 B2 | 3/2014 | Goldboss et al. |
| 8,672,951 B2 | 3/2014 | Smith et al. |
| 8,678,264 B2 | 3/2014 | Racenet et al. |
| 8,679,137 B2 | 3/2014 | Bauman et al. |
| 8,684,248 B2 | 4/2014 | Milliman |
| 8,684,250 B2 | 4/2014 | Bettuchi et al. |
| 8,684,251 B2 | 4/2014 | Rebuffat et al. |
| 8,684,252 B2 | 4/2014 | Patel et al. |
| 8,695,864 B1 | 4/2014 | Hausen |
| 8,708,212 B2 | 4/2014 | Williams |
| 8,733,611 B2 | 5/2014 | Milliman |
| 8,733,614 B2 * | 5/2014 | Ross ............... A61B 17/068 227/179.1 |
| 8,733,615 B2 | 5/2014 | Nalagatla et al. |
| 8,746,531 B2 | 6/2014 | Wenchell et al. |
| 8,746,532 B2 | 6/2014 | Nalagatla et al. |
| 8,783,543 B2 | 7/2014 | Shelton, IV et al. |
| 8,789,737 B2 | 7/2014 | Hodgkinson et al. |
| 8,800,838 B2 | 8/2014 | Shelton, IV |
| 8,800,841 B2 | 8/2014 | Ellerhorst et al. |
| 8,801,734 B2 | 8/2014 | Shelton, IV et al. |
| 8,801,735 B2 | 8/2014 | Shelton, IV et al. |
| 8,821,523 B2 | 9/2014 | Heinrich et al. |
| 8,827,903 B2 | 9/2014 | Shelton, IV et al. |
| 8,833,629 B2 | 9/2014 | Nalagatla et al. |
| 8,840,004 B2 | 9/2014 | Holsten et al. |
| 8,844,792 B2 | 9/2014 | Viola |
| 8,845,661 B2 | 9/2014 | D'Arcangelo et al. |
| 8,870,911 B2 | 10/2014 | Williams et al. |
| 8,875,974 B2 | 11/2014 | Rebuffat et al. |
| 8,893,948 B2 | 11/2014 | Williams |
| 8,910,847 B2 | 12/2014 | Nalagatla et al. |
| 8,925,785 B2 | 1/2015 | Holsten et al. |
| 8,925,786 B2 | 1/2015 | Holsten et al. |
| 8,967,448 B2 | 3/2015 | Carter et al. |
| 8,978,955 B2 | 3/2015 | Aronhalt et al. |
| 9,010,608 B2 | 4/2015 | Casasanta, Jr. et al. |
| 9,010,612 B2 | 4/2015 | Stevenson et al. |
| 9,016,540 B2 | 4/2015 | Whitman et al. |
| 9,033,204 B2 | 5/2015 | Shelton, IV et al. |
| 9,095,340 B2 | 8/2015 | Felder et al. |
| 9,113,871 B2 | 8/2015 | Milliman et al. |
| 9,113,877 B1 | 8/2015 | Whitman et al. |
| 9,113,883 B2 | 8/2015 | Aronhalt et al. |
| 9,113,884 B2 | 8/2015 | Shelton, IV et al. |
| 9,113,885 B2 | 8/2015 | Hodgkinson et al. |
| 9,125,654 B2 | 9/2015 | Aronhalt et al. |
| 9,155,536 B1 | 10/2015 | Hausen et al. |
| 9,161,757 B2 | 10/2015 | Bettuchi |
| 9,204,881 B2 | 12/2015 | Penna |
| 9,211,122 B2 | 12/2015 | Hagerty et al. |
| 9,220,504 B2 | 12/2015 | Viola et al. |
| 9,232,941 B2 | 1/2016 | Mandakolathur Vasudevan et al. |
| 9,232,945 B2 | 1/2016 | Zingman |
| 9,289,207 B2 | 3/2016 | Shelton, IV |
| 9,301,763 B2 | 4/2016 | Qiao et al. |
| 9,307,994 B2 | 4/2016 | Gresham et al. |
| 9,326,773 B2 | 5/2016 | Casasanta, Jr. et al. |
| 9,351,729 B2 | 5/2016 | Orban, III et al. |

(56) References Cited

U.S. PATENT DOCUMENTS

| | | |
|---|---|---|
| 9,351,731 B2 | 5/2016 | Carter et al. |
| 9,364,229 B2 | 6/2016 | D'Agostino et al. |
| 9,370,366 B2 | 6/2016 | Mozdzierz |
| 9,370,367 B2 | 6/2016 | Mozdzierz |
| 9,393,014 B2 | 7/2016 | Milliman |
| 9,408,603 B2 | 8/2016 | Patel |
| 9,421,013 B2 | 8/2016 | Patel et al. |
| 9,445,817 B2 | 9/2016 | Bettuchi |
| 9,451,962 B2 | 9/2016 | Olson |
| 9,456,821 B2 | 10/2016 | Bettuchi et al. |
| 9,463,022 B2 | 10/2016 | Swayze et al. |
| 9,492,166 B2 | 11/2016 | Kostrzewski |
| 9,498,222 B2 | 11/2016 | Scheib et al. |
| 9,504,470 B2 | 11/2016 | Milliman |
| 9,522,005 B2 | 12/2016 | Williams et al. |
| 9,549,738 B2 | 1/2017 | Mandakolathur Vasudevan et al. |
| 9,572,572 B2 | 2/2017 | Williams |
| 9,579,102 B2 | 2/2017 | Holsten et al. |
| 9,592,055 B2 | 3/2017 | Milliman et al. |
| 9,592,056 B2 | 3/2017 | Mozdzierz et al. |
| 9,597,081 B2 | 3/2017 | Swayze et al. |
| 9,597,082 B2 | 3/2017 | Stokes et al. |
| 9,603,599 B2 | 3/2017 | Miller et al. |
| 9,629,624 B2 | 4/2017 | Hessler et al. |
| 9,636,112 B2 | 5/2017 | Penna et al. |
| 9,649,110 B2 | 5/2017 | Parihar et al. |
| 9,649,113 B2 | 5/2017 | Ma et al. |
| 9,668,740 B2 | 6/2017 | Williams |
| 9,675,348 B2 | 6/2017 | Smith et al. |
| 9,681,872 B2 | 6/2017 | Jankowski et al. |
| 9,681,873 B2 | 6/2017 | Smith et al. |
| 9,687,234 B2 | 6/2017 | Smith et al. |
| 9,693,773 B2 | 7/2017 | Williams |
| 9,700,309 B2 | 7/2017 | Jaworek |
| 9,706,999 B2 | 7/2017 | Motai |
| 9,713,469 B2 | 7/2017 | Leimbach et al. |
| 9,737,304 B2 | 8/2017 | Bettuchi et al. |
| 9,743,955 B2 | 8/2017 | Hill et al. |
| 9,750,503 B2 | 9/2017 | Milliman |
| 9,763,663 B2 | 9/2017 | Weisshaupt et al. |
| 9,801,626 B2 | 10/2017 | Parihar et al. |
| 9,833,235 B2 | 12/2017 | Penna et al. |
| 9,844,368 B2 | 12/2017 | Boudreaux et al. |
| 9,861,368 B2 | 1/2018 | Racenet et al. |
| 9,883,862 B2 | 2/2018 | Rebuffat et al. |
| 9,907,600 B2 | 3/2018 | Stulen et al. |
| 10,039,549 B2 | 8/2018 | Williams |
| 10,085,744 B2 | 10/2018 | Williams et al. |
| 10,105,137 B2 | 10/2018 | Holsten et al. |
| 10,117,655 B2 | 11/2018 | Scirica et al. |
| 10,117,656 B2 | 11/2018 | Sgroi, Jr. |
| 10,136,888 B2 | 11/2018 | Chen et al. |
| 10,149,680 B2 | 12/2018 | Parihar et al. |
| 10,154,845 B2 | 12/2018 | Williams |
| 10,172,622 B2 | 1/2019 | Kelley |
| 10,178,994 B2 | 1/2019 | Lee et al. |
| 10,188,386 B2 | 1/2019 | Measamer et al. |
| 10,190,888 B2 | 1/2019 | Hryb et al. |
| 10,194,911 B2 | 2/2019 | Miller et al. |
| 10,226,253 B2 | 3/2019 | DiNardo et al. |
| 10,245,038 B2 | 4/2019 | Hopkins et al. |
| 10,271,842 B2 | 4/2019 | Fox et al. |
| 10,271,843 B2 | 4/2019 | Shi et al. |
| 10,307,157 B2 | 6/2019 | Miller et al. |
| 10,321,908 B2 | 6/2019 | Carter et al. |
| 10,327,779 B2 | 6/2019 | Richard et al. |
| 10,342,629 B2 | 7/2019 | Penna et al. |
| 10,405,855 B2 | 9/2019 | Stager et al. |
| 10,413,299 B2 | 9/2019 | Milliman |
| 10,426,468 B2 | 10/2019 | Contini et al. |
| 10,426,480 B2 | 10/2019 | Scirica et al. |
| 10,433,848 B2 | 10/2019 | Chen et al. |
| 10,456,134 B2 | 10/2019 | DiNardo et al. |
| 10,463,365 B2 | 11/2019 | Williams |
| 10,463,373 B2 | 11/2019 | Mozdzierz et al. |
| 10,463,374 B2 | 11/2019 | Sgroi, Jr. |
| 10,470,770 B2 | 11/2019 | Shelton, IV et al. |
| 10,470,771 B2 | 11/2019 | D'Agostino et al. |
| 10,499,922 B2 | 12/2019 | Sgroi, Jr. |
| 10,506,920 B2 | 12/2019 | Hasser et al. |
| 10,507,039 B2 | 12/2019 | Williams |
| 10,512,467 B2 | 12/2019 | Swayze et al. |
| 10,524,795 B2 | 1/2020 | Nalagatla et al. |
| 10,524,798 B2 | 1/2020 | Williams |
| 10,524,868 B2 | 1/2020 | Cooper et al. |
| 10,537,331 B2 | 1/2020 | Scirica et al. |
| 10,542,993 B2 | 1/2020 | Guerrera et al. |
| 10,548,598 B2 | 2/2020 | Prescott et al. |
| 10,561,424 B2 | 2/2020 | Penna et al. |
| 10,568,631 B2 | 2/2020 | Rebuffat et al. |
| 10,575,847 B2 | 3/2020 | Hessler et al. |
| 10,595,871 B2 | 3/2020 | Racenet et al. |
| 10,595,872 B2 | 3/2020 | Milliman |
| 10,603,042 B2 | 3/2020 | Sgroi |
| 10,624,646 B2 | 4/2020 | Bae et al. |
| 10,639,041 B2 | 5/2020 | Williams |
| 10,653,414 B2 | 5/2020 | Williams |
| 10,758,230 B2* | 9/2020 | Shelton, IV ...... A61B 17/07207 |
| 10,898,196 B2 | 1/2021 | Sapienza et al. |
| 11,076,853 B2* | 8/2021 | Parfett ............. A61B 17/07207 |
| 11,364,029 B2* | 6/2022 | Burbank .......... A61B 17/07207 |
| 2003/0111507 A1 | 6/2003 | Nunez |
| 2003/0125717 A1* | 7/2003 | Whitman ................ A61B 90/98 |
| | | 606/1 |
| 2005/0051597 A1 | 3/2005 | Toledano |
| 2005/0107813 A1 | 5/2005 | Gilete Garcia |
| 2006/0000869 A1 | 1/2006 | Fontayne |
| 2006/0011698 A1 | 1/2006 | Okada et al. |
| 2006/0201989 A1 | 9/2006 | Ojeda |
| 2006/0278680 A1* | 12/2006 | Viola ................... A61B 17/072 |
| | | 227/176.1 |
| 2007/0027473 A1 | 2/2007 | Vresh et al. |
| 2007/0029363 A1 | 2/2007 | Popov |
| 2007/0060952 A1 | 3/2007 | Roby et al. |
| 2007/0084898 A1* | 4/2007 | Scirica ............. A61B 17/07207 |
| | | 227/176.1 |
| 2009/0090763 A1* | 4/2009 | Zemlok ............ A61B 17/07207 |
| | | 227/175.2 |
| 2009/0236392 A1 | 9/2009 | Cole et al. |
| 2009/0236398 A1 | 9/2009 | Cole et al. |
| 2009/0236401 A1 | 9/2009 | Cole et al. |
| 2010/0019016 A1 | 1/2010 | Edoga et al. |
| 2010/0051668 A1 | 3/2010 | Milliman et al. |
| 2010/0084453 A1 | 4/2010 | Hu |
| 2010/0163598 A1 | 7/2010 | Belzer |
| 2010/0224668 A1 | 9/2010 | Fontayne et al. |
| 2010/0230465 A1 | 9/2010 | Smith et al. |
| 2011/0011916 A1 | 1/2011 | Levine |
| 2011/0017801 A1* | 1/2011 | Zemlok ............ A61B 17/07207 |
| | | 227/175.1 |
| 2011/0114697 A1 | 5/2011 | Baxter, III et al. |
| 2011/0114700 A1 | 5/2011 | Baxter, III et al. |
| 2011/0144640 A1 | 6/2011 | Heinrich et al. |
| 2011/0192882 A1 | 8/2011 | Hess et al. |
| 2012/0138658 A1* | 6/2012 | Ullrich .................. A61B 34/76 |
| | | 227/175.1 |
| 2012/0145755 A1 | 6/2012 | Kahn |
| 2012/0193395 A1 | 8/2012 | Pastorelli et al. |
| 2012/0193398 A1 | 8/2012 | Williams et al. |
| 2012/0232339 A1 | 9/2012 | Csiky |
| 2012/0273548 A1 | 11/2012 | Ma et al. |
| 2013/0020372 A1 | 1/2013 | Jankowski et al. |
| 2013/0020373 A1 | 1/2013 | Smith et al. |
| 2013/0032628 A1 | 2/2013 | Li et al. |
| 2013/0060258 A1 | 3/2013 | Giacomantonio |
| 2013/0105544 A1 | 5/2013 | Mozdzierz et al. |
| 2013/0105551 A1 | 5/2013 | Zingman |
| 2013/0126580 A1 | 5/2013 | Smith et al. |
| 2013/0153631 A1 | 6/2013 | Vasudevan et al. |
| 2013/0175315 A1 | 7/2013 | Milliman |
| 2013/0175318 A1 | 7/2013 | Felder et al. |
| 2013/0181035 A1 | 7/2013 | Milliman |
| 2013/0181036 A1 | 7/2013 | Olson et al. |
| 2013/0193190 A1 | 8/2013 | Carter et al. |

(56) References Cited

U.S. PATENT DOCUMENTS

| | | |
|---|---|---|
| 2013/0200131 A1 | 8/2013 | Racenet et al. |
| 2013/0206816 A1 | 8/2013 | Penna |
| 2013/0240597 A1 | 9/2013 | Milliman et al. |
| 2013/0277411 A1 | 10/2013 | Hodgkinson et al. |
| 2013/0284792 A1 | 10/2013 | Ma |
| 2014/0008413 A1 | 1/2014 | Williams |
| 2014/0046352 A1 | 2/2014 | Reboa et al. |
| 2014/0158747 A1 | 6/2014 | Measamer et al. |
| 2014/0284370 A1 | 9/2014 | Sahin |
| 2015/0083772 A1 | 3/2015 | Miller et al. |
| 2015/0173763 A1 | 6/2015 | Liu |
| 2015/0209045 A1 | 7/2015 | Hodgkinson et al. |
| 2016/0066916 A1* | 3/2016 | Overmyer ............ G06F 1/3287 227/176.1 |
| 2016/0132026 A1* | 5/2016 | Wingardner ............ G05B 9/02 700/275 |
| 2017/0128068 A1 | 5/2017 | Zhang et al. |
| 2017/0296191 A1* | 10/2017 | Shelton, IV ..... A61B 17/07207 |
| 2018/0168651 A1* | 6/2018 | Shelton, IV ..... A61B 17/07207 |
| 2018/0353186 A1* | 12/2018 | Mozdzierz ........... A61B 17/072 |
| 2019/0200989 A1* | 7/2019 | Burbank .......... A61B 17/07207 |
| 2020/0367891 A1 | 11/2020 | Kollar et al. |
| 2022/0022877 A1* | 1/2022 | Strassner ............... A61B 90/06 |
| 2023/0240684 A1* | 8/2023 | Strassner ........... A61B 17/1155 227/179.1 |

FOREIGN PATENT DOCUMENTS

| | | | |
|---|---|---|---|
| CN | 104039244 | A | 9/2014 |
| CN | 104042288 | A | 9/2014 |
| CN | 104367360 | A | 2/2015 |
| DE | 1057729 | B | 5/1959 |
| DE | 3301713 | A1 | 7/1984 |
| EP | 0152382 | A2 | 8/1985 |
| EP | 0173451 | A1 | 3/1986 |
| EP | 0190022 | A2 | 8/1986 |
| EP | 0282157 | A1 | 9/1988 |
| EP | 0503689 | A2 | 9/1992 |
| EP | 1354560 | A2 | 10/2003 |
| EP | 1671597 | A1 | 6/2006 |
| EP | 2138118 | A2 | 12/2009 |
| EP | 2168510 | A1 | 3/2010 |
| EP | 2238926 | A2 | 10/2010 |
| EP | 2524656 | A2 | 11/2012 |
| EP | 3023077 | A1 | 5/2016 |
| EP | 3412225 | A1 | 12/2018 |
| EP | 3412226 | A1 | 12/2018 |
| EP | 3549545 | A2 | 10/2019 |
| FR | 1136020 | A | 5/1957 |
| FR | 1461464 | A | 2/1966 |
| FR | 1588250 | A | 4/1970 |
| FR | 2443239 | A1 | 7/1980 |
| GB | 1185292 | A | 3/1970 |
| GB | 2016991 | A | 9/1979 |
| GB | 2070499 | A | 9/1981 |
| JP | 2004147969 | A | 5/2004 |
| JP | 2013138860 | A | 7/2013 |
| NL | 7711347 | A | 4/1979 |
| SU | 1509052 | A1 | 9/1989 |
| WO | 8706448 | A1 | 11/1987 |
| WO | 8900406 | A1 | 1/1989 |
| WO | 9006085 | A1 | 6/1990 |
| WO | 9835614 | A1 | 8/1998 |
| WO | 0154594 | A1 | 8/2001 |
| WO | 02080781 | A2 | 10/2002 |
| WO | 2004047654 | A2 | 6/2004 |
| WO | 2008107918 | A1 | 9/2008 |
| WO | 2019130087 | A1 | 7/2019 |

OTHER PUBLICATIONS

Extended European Search Report from Appl. No. 14181908.6 dated May 26, 2015.
European Examination Report from Appl. No. 14181908.6 dated May 3, 2016.
International Search Report and Written Opinion of the International Searching Authority issued in corresponding application PCT/IB2022/061586 mailed Feb. 16, 2023 (13 pages).

* cited by examiner

DETERMINATION OF PREMATURE STAPLE EJECTION

BACKGROUND

1. Technical Field

The present disclosure relates to surgical devices. More specifically, the present disclosure relates to handheld electromechanical surgical systems for performing surgical procedures.

2. Background of Related Art

Circular staplers are used in a surgical procedure to reattach rectum portions that were previously transected, or similar procedures. Conventional circular clamping, cutting and stapling instruments include a pistol or linear grip-styled structure having an elongated shaft extending therefrom and a staple cartridge supported on the distal end of the elongated shaft. In this instance, a physician may insert an anvil assembly of the circular stapling instrument into a rectum of a patient and maneuver the anvil assembly up the colonic tract of the patient toward the transected rectum portions. The physician may also insert the remainder of the circular stapling instrument (including the cartridge assembly) through an incision and toward the transected rectum portions. The anvil and cartridge assemblies are approximated toward one another, and staples are ejected from the cartridge assembly toward the anvil assembly to form the staples in tissue to affect an end-to-end anastomosis, and an annular knife is advanced to core a portion of the clamped tissue portions. After the end-to-end anastomosis has been affected, the circular stapling apparatus is removed from the surgical site.

Powered surgical staplers have been developed and utilize one or more motors to clamp, cut, and staple tissue. The powered surgical staplers may include a powered handle assembly and an adapter assembly, which are reusable, and a disposable staple cartridge assembly, i.e., reload, that is selectively connected to the adapter assembly prior to use. The adapter assembly includes multiple transmission assemblies, e.g., drive shafts, which transmit actuation from the powered handle to the disposable staple cartridge. The powered surgical staplers operate in three sequences, namely, clamping, stapling, and cutting. Clamping approximates tissue grasped between an anvil and a cartridge assembly and compresses the tissue. This sequence prepares the tissue to receive staples. Occasionally, staples disposed in the reload may be partially ejected, e.g., being pushed proud by the drive shafts of the adapter assembly. Pushing staples prior to the stapling process may result in malformed staples.

SUMMARY

The present disclosure provides a powered circular stapler is configured to operate in three sequences, namely, clamping, stapling, and cutting to form an anastomosis by connecting two portions of a structure (e.g., intestine, colon, etc.). The powered circular stapler includes a handle assembly having a power source and one or more motors coupled to the power source. The stapler also includes an adapter assembly having one or more drive mechanisms actuated by the motors and a reload including a plurality of staples ejectable by the drive mechanisms against an anvil. The stapler is configured to calibrate the adapter assembly and determine whether the staples of the reload were previously ejected based on a travel distance of one or more drive mechanisms to reach a hard stop. If the travel distance is above a threshold, then the stapler determines that the staples have been partially pushed, and the reload is marked as used, which prevents any use of the reload since such a marking is read by the stapler prior to using the reload during a surgical procedure.

According to one embodiment of the present disclosure, a surgical device is disclosed. The surgical device includes a power source, a motor coupled to the power source, and a transmission assembly movable by the motor. The device also includes a reload coupled to the transmission assembly. The reload includes a plurality of staples ejectable by the transmission assembly. The device further include a distance sensor configured to monitor operation of the transmission assembly and output distance data. The device additionally includes a controller configured to operate the motor to move the transmission assembly proximally from a distal position until a hard stop is reached, and determine whether the plurality of staples have been previously ejected based on the distance data.

Implementations of the above embodiment may include one or more of the following features. According to one aspect of the above embodiment, the reload may include a storage device. The controller is further configured to update a status of the reload stored on the storage device in response to a determination that the plurality of staples have been previously ejected. The controller may be further configured to determine a distance travelled by the transmission assembly to reach a hard stop based on the distance data. The controller may be further configured to compare the distance travelled by the transmission assembly to reach the hard stop to a threshold distance. The controller may be also configured to determine that the plurality of staples have been previously ejected based on the distance travelled by the transmission assembly to reach the hard stop exceeding the threshold distance. The surgical device may also include a current sensor configured to measure a current draw of the motor. The controller may be further configured to determine the transmission assembly reaching the hard stop based on the current draw of the motor.

According to another embodiment of the present disclosure, a surgical device is disclosed. The surgical device includes an adapter assembly having a transmission assembly and a reload coupled to the transmission assembly, the reload may include a plurality of staples ejectable by the transmission assembly. The surgical device also includes a handle assembly having a power source and a motor coupled to the power source, the motor is configured to move the transmission assembly. The handle assembly also includes a distance sensor configured to monitor operation of the transmission assembly and output distance data. The device further includes a controller configured to operate the motor to move the transmission assembly proximally from a distal position until a hard stop is reached, and determine whether the plurality of staples have been previously ejected based on the distance data.

Implementations of the above embodiment may include one or more of the following features. According to one aspect of the above embodiment, the reload may include a storage device. The controller is further configured to update a status of the reload stored on the storage device in response to a determination that the plurality of staples have been previously ejected. The controller may be further configured to determine a distance travelled by the transmission assembly to reach a hard stop based on the distance data. The controller may be further configured to compare the distance travelled by the transmission assembly to reach the hard stop to a threshold distance. The controller may be also configured to determine that the plurality of staples have been previously ejected based on the distance travelled by the transmission assembly to reach the hard stop exceeding the threshold distance. The surgical device may also include a current sensor configured to measure a current draw of the motor. The controller may be further configured to determine the transmission assembly reaching the hard stop based on the current draw of the motor.

According to a further embodiment of the present disclosure, a method for operating a powered surgical device is disclosed. The method includes operating a motor to move a transmission assembly proximally from a distal position until a hard stop is reached. The transmission assembly is configured to eject a plurality of staples disposed within a reload coupled to the transmission assembly. The method also includes measuring a distance travelled by the transmission assembly. The method further includes determining whether the plurality of staples have been previously ejected based on the distance travelled by the transmission assembly to reach a hard stop.

Implementations of the above embodiment may include one or more of the following features. According to one aspect of the above embodiment, the method may also include updating a status of the reload stored on a storage device in response to determining that the plurality of staples have been previously ejected. The method may further include determining that the plurality of staples have been previously ejected may include comparing the distance travelled by the transmission assembly to reach the hard stop to a threshold distance. The method may additionally include determining that the transmission assembly reached the hard stop based on a current draw of the motor.

BRIEF DESCRIPTION OF THE DRAWINGS

Embodiments of the present disclosure are described herein with reference to the accompanying drawings, wherein.

DETAILED DESCRIPTION OF EMBODIMENTS

Figure 1:
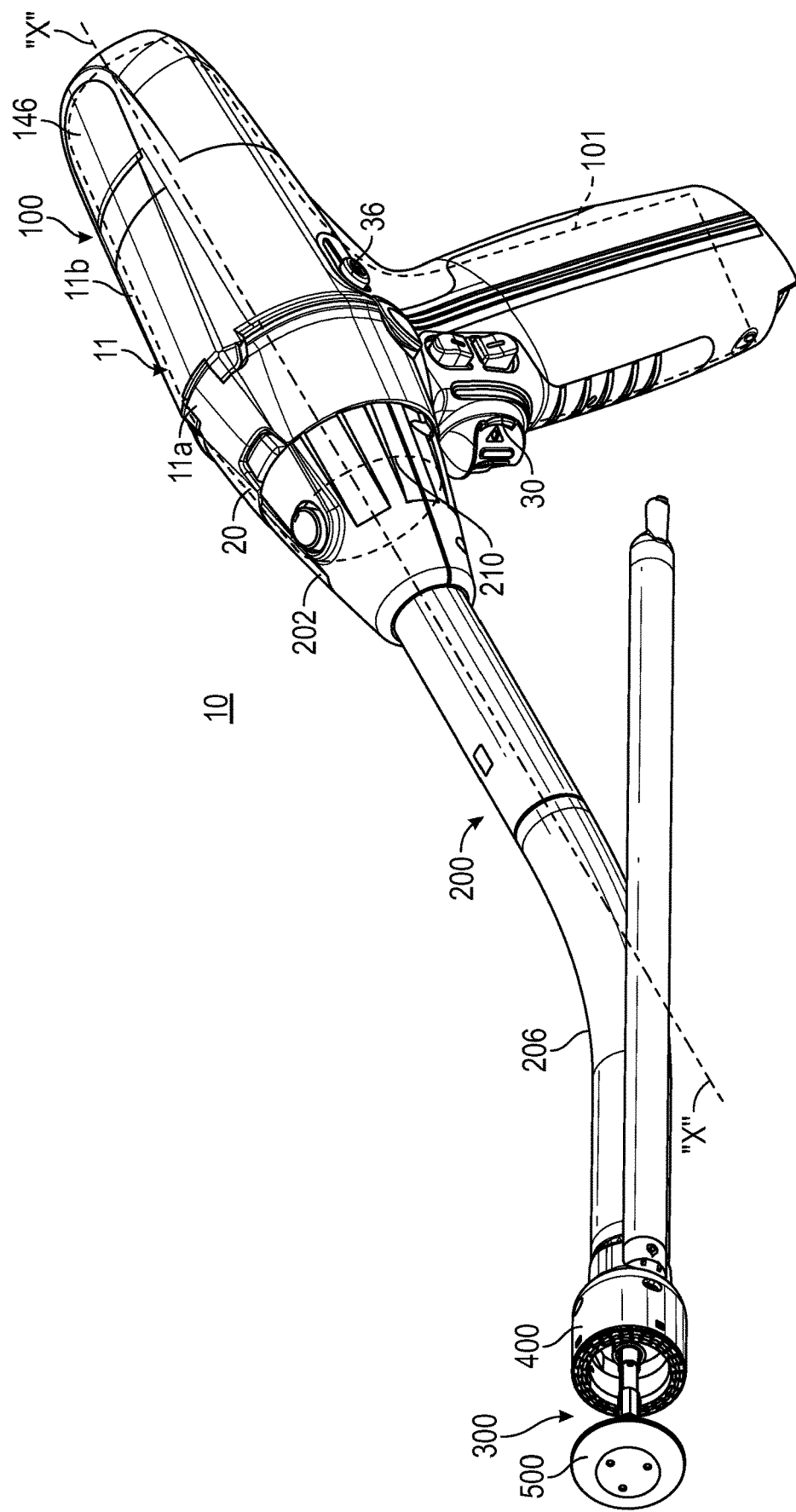
FIG. 1 is a perspective view of a powered circular stapler including a handle assembly, an adapter assembly, and an end effector, according to an embodiment of the present disclosure.

Embodiments of the presently disclosed surgical devices, and adapter assemblies for surgical devices and/or handle assemblies are described in detail with reference to the drawings, in which like reference numerals designate identical or corresponding elements in each of the several views. As used herein the term "distal" refers to that portion of the surgical instrument, or component thereof, farther from the user, while the term "proximal" refers to that portion of the surgical instrument, or component thereof, closer to the user.

The present disclosure provides a powered circular stapler 10 having a handle assembly, an adapter assembly coupled to the handle assembly, and an end effector coupled to the adapter assembly. The stapler allows for full, independent control of three functions: clamping, stapling, and cutting. FIG. 1 illustrates a surgical device, such as, for example, a powered circular stapler 10 for forming end-to-end anastomosis ("EEA"), including a handle assembly 100, which is configured for selective connection with an adapter assembly 200. The adapter assembly 200 is configured for selective connection with an end effector 300, which includes a reload 400 and an anvil assembly 500. The end effector 300 is configured to produce a surgical effect on tissue of a patient, namely, forming an anastomosis by connecting two portions of a structure (e.g., intestine, colon, etc.) by clamping, stapling, and cutting tissue grasped within the end effector 300.

The handle assembly 100 includes a power handle 101 and an outer shell housing 11 configured to selectively receive and encase power handle 101. The shell housing 11 includes a distal half-section 11a and a proximal half-section 11b pivotably connected to distal half-section 11a. When joined, distal and proximal half-sections 11a, 11b define a shell cavity therein in which power handle 101 is disposed.

While the powered circular stapler 10 is described herein as a modular device including a plurality of interconnected components, such as the handle assembly 100, the removable shell housing 11, and the adapter assembly 200, etc. The powered circular stapler 10 may be formed as an integrated device with one or more of the components being securely attached to each other, e.g., during manufacturing of the powered circular stapler.

Distal and proximal half-sections 11a, 11b of shell housing 11 are divided along a plane that traverses a longitudinal axis "X" of adapter assembly 200. Distal half-section 11a of shell housing 11 defines a connecting portion 20 configured to accept a corresponding drive coupling assembly 210 (FIG. 3) of adapter assembly 200. Distal half-section 11a of shell housing 11 supports a toggle control button 30. Toggle control button 30 is capable of being actuated in four directions (e.g., a left, right, up and down).

Figure 2:
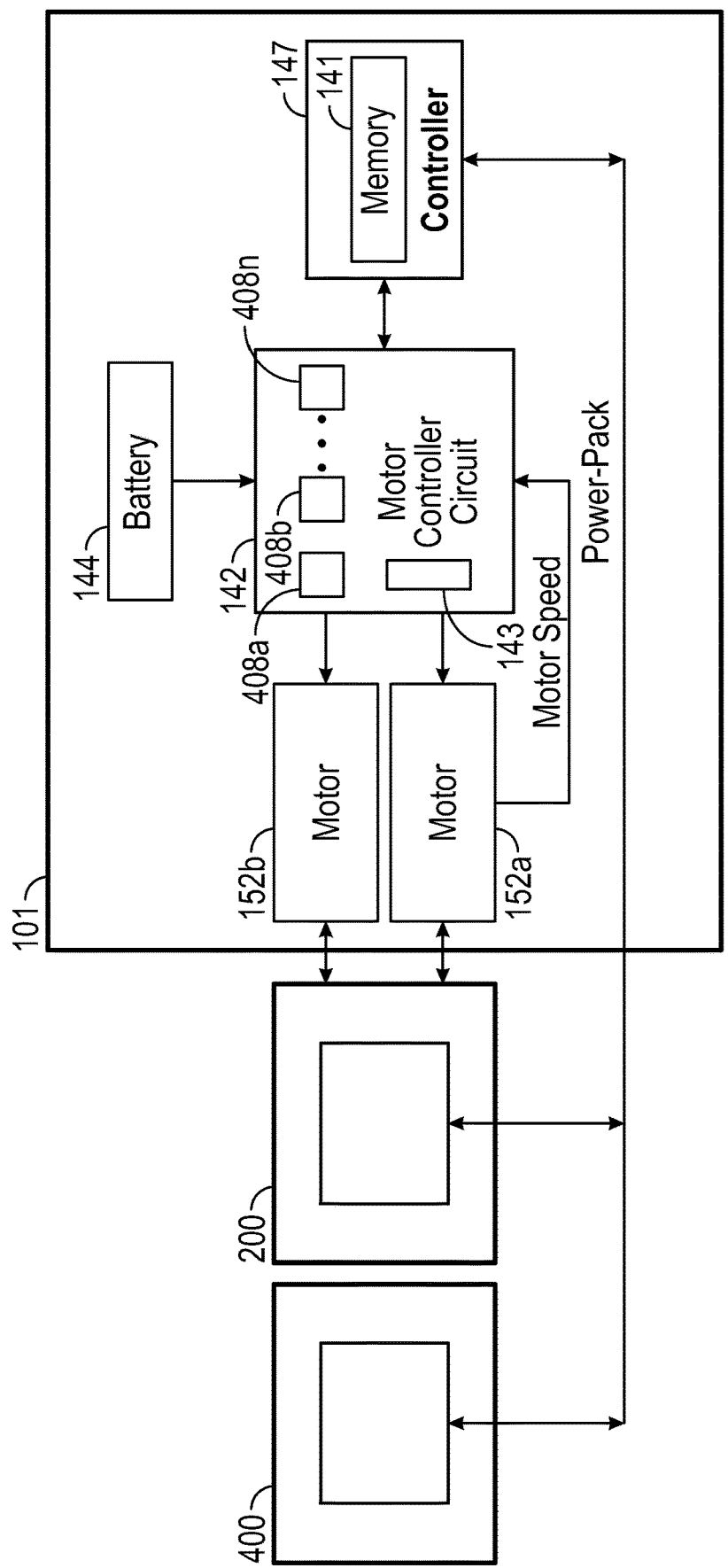
FIG. 2 is a schematic diagram of the handle assembly, the adapter assembly, and the end effector of FIG. 1.

With reference to FIGS. 1 and 2, the power handle 101 includes a main controller circuit board 142, a rechargeable battery 144 configured to supply power to any of the electrical components of handle assembly 100, and a plurality of motors, i.e., a first motor 152a, a second motor 152b coupled to the battery 144. The power handle 101 also includes a display 146. In embodiments, the motors 152*a* and 152*b* may be coupled to any suitable power source configured to provide electrical energy to the motors 152*a* and 152*b*, such as an AC/DC transformer. Each of the motors 152*a* and 152*b* is coupled a motor controller 143 which controls the operation of the corresponding motors 152*a* and 152*b* including the flow of electrical energy from the battery 144 to the motors 152*a* and 152*b*. A main controller 147 is provided that controls the power handle 101. The main controller 147 is configured to execute software instructions embodying algorithms disclosed herein, such as clamping, stapling, and cutting algorithms which control operation of the power handle 101.

The motor controller 143 includes a plurality of sensors 408*a* . . . 408*n* configured to measure operational states of the motors 152*a* and 152*b* and the battery 144. The sensors 408*a*-*n* include a strain gauge 408*b* and may also include voltage sensors, current sensors, temperature sensors, telemetry sensors, optical sensors, and combinations thereof. The sensors 408*a*-408*n* may measure voltage, current, and other electrical properties of the electrical energy supplied by the battery 144. The sensors 408*a*-408*n* may also measure angular velocity (e.g., rotational speed) as revolutions per minute (RPM), torque, temperature, current draw, and other operational properties of the motors 152*a* and 152*b*. The sensor 408*a* also includes an encoder configured to count revolutions or other indicators of the motors 152*a* and 152*b*, which is then used by the main controller 147 to calculate linear movement of components movable by the motors 152*a* and 152*b*. Angular velocity may be determined by measuring the rotation of the motors 152*a* and 152*b* or a drive shaft (not shown) coupled thereto and rotatable by the motors 152*a* and 152*b*. The position of various axially movable drive shafts may also be determined by using various linear sensors disposed in or in proximity to the shafts or extrapolated from the RPM measurements. In embodiments, torque may be calculated based on the regulated current draw of the motors 152*a* and 152*b* at a constant RPM. In further embodiments, the motor controller 143 and/or the main controller 147 may measure time and process the above-described values as a function of time, including integration and/or differentiation, e.g., to determine the rate of change in the measured values. The main controller 147 is also configured to determine distance traveled of various components of the adapter assembly 200 and/or the end effector 300 by counting revolutions of the motors 152*a* and 152*b*.

The motor controller 143 is coupled to the main controller 147, which includes a plurality of inputs and outputs for interfacing with the motor controller 143. In particular, the main controller 147 receives measured sensor signals from the motor controller 143 regarding operational status of the motors 152*a* and 152*b* and the battery 144 and, in turn, outputs control signals to the motor controller 143 to control the operation of the motors 152*a* and 152*b* based on the sensor readings and specific algorithm instructions. The main controller 147 is also configured to accept a plurality of user inputs from a user interface (e.g., switches, buttons, touch screen, etc. coupled to the main controller 147).

The main controller 147 is also coupled to a memory 141. The memory 141 may include volatile (e.g., RAM) and non-volatile storage configured to store data, including software instructions for operating the power handle 101. The main controller 147 is also coupled to the strain gauge 408*b* of the adapter assembly 200 using a wired or a wireless connection and is configured to receive strain measurements from the strain gauge 408*b* which are used during operation of the power handle 101.

The power handle 101 includes a plurality of motors 152*a* and 152*b* each including a respective motor shaft (not explicitly shown) extending therefrom and configured to drive a respective transmission assembly. Rotation of the motor shafts by the respective motors function to drive shafts and/or gear components of adapter assembly 200 in order to perform the various operations of handle assembly 100. In particular, motors 152*a* and 152*b* of power handle 101 are configured to drive shafts and/or gear components of adapter assembly 200 in order to selectively extend/retract a trocar member 274 (FIG. 4) of a trocar assembly 270 of adapter assembly 200. Extension/retraction of the trocar member 274 opens/closes end effector 300 (when anvil assembly 500 is connected to trocar member 274 of trocar assembly 270), fire an annular array of staples 423 of reload 400, and move an annular knife 444 of reload 400.

Figure 3:
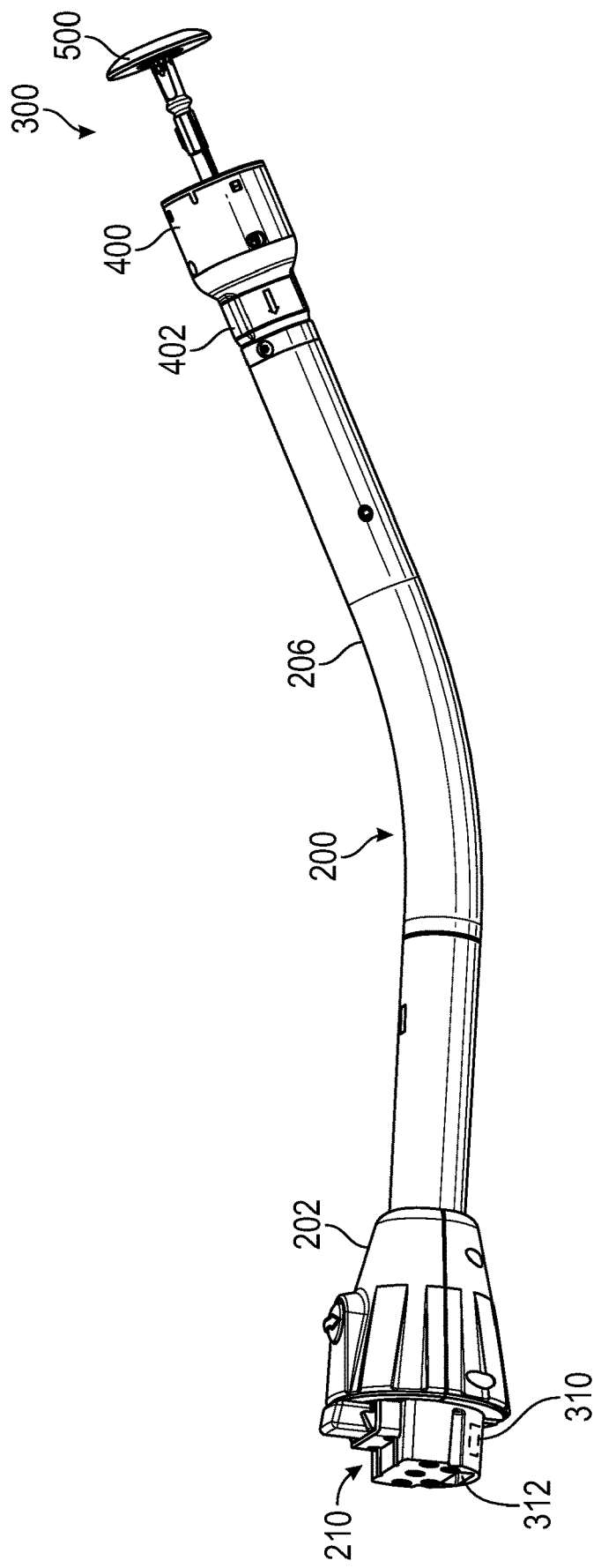
FIG. 3 is a side perspective view of the adapter assembly and the end effector, an annular reload and an anvil assembly, attached to the adapter assembly of FIG. 1 according to an embodiment of the present disclosure.
Figure 4:
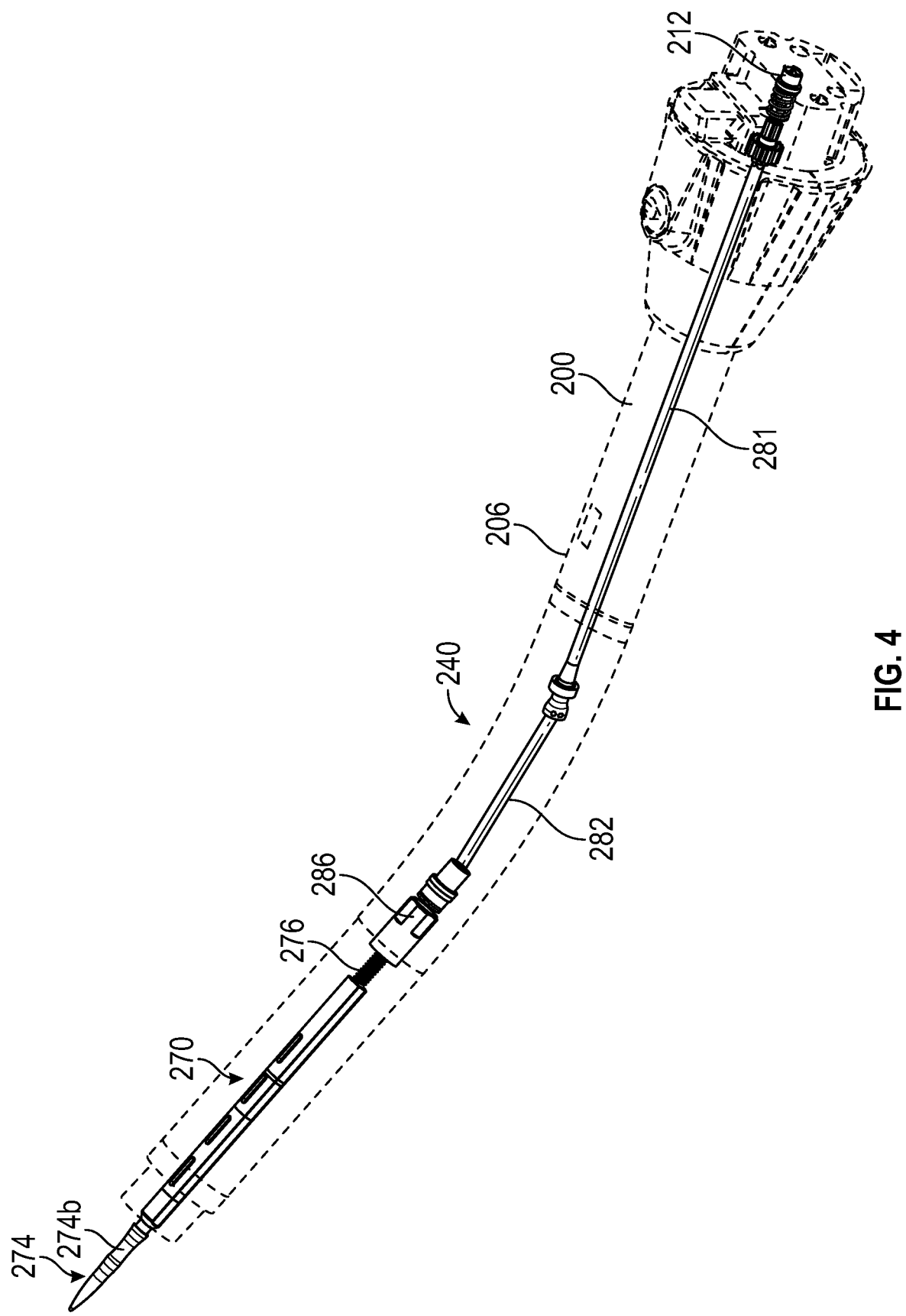
FIG. 4 is a perspective view of a clamping transmission assembly disposed within the adapter assembly of FIG. 1, shown partially in phantom.

Turning now to FIGS. 3 and 4, adapter assembly 200 includes an outer knob housing 202 and an outer tube 206 extending from a distal end of knob housing 202. Knob housing 202 and outer tube 206 are configured and dimensioned to house the components of adapter assembly 200. The knob housing 202 includes an electrical connector 312 and a storage device 310 coupled thereto. The storage device 310 is configured to store various operating parameters pertaining to the adapter assembly 200. Adapter assembly 200 is configured to convert rotation of coupling shafts (not explicitly shown) of handle assembly 100 into axial translations useful for operating trocar assembly 270 of adapter assembly 200, anvil assembly 500, and/or staple driver 430 or knife assembly 440 of reload 400.

Adapter assembly 200 further includes the trocar assembly 270 removably supported in a distal end of outer tube 206. Trocar assembly 270 includes a trocar member 274 and a drive screw 276 operably received within trocar member 274 for axially moving trocar member 274 relative to outer tube 206. A distal end 274*b* of trocar member 274 is configured to selectively engage anvil assembly 500, such that axial movement of trocar member 274, via a rotation of drive screw 276, results in a concomitant axial movement of anvil assembly 500.

With reference to FIG. 4, a clamping transmission assembly 240 includes first rotatable proximal drive shaft 212 coupled to one of the motors 152*a* and 152*b*, a second rotatable proximal drive shaft 281, a rotatable distal drive shaft 282, and a coupling member 286, each of which are supported within the outer tube 206 of adapter assembly 200. Clamping transmission assembly 240 functions to extend/retract trocar member 274 of trocar assembly 270 of adapter assembly 200, and to open/close the anvil assembly 510 when anvil assembly 510 is connected to trocar member 274.

Figure 5:
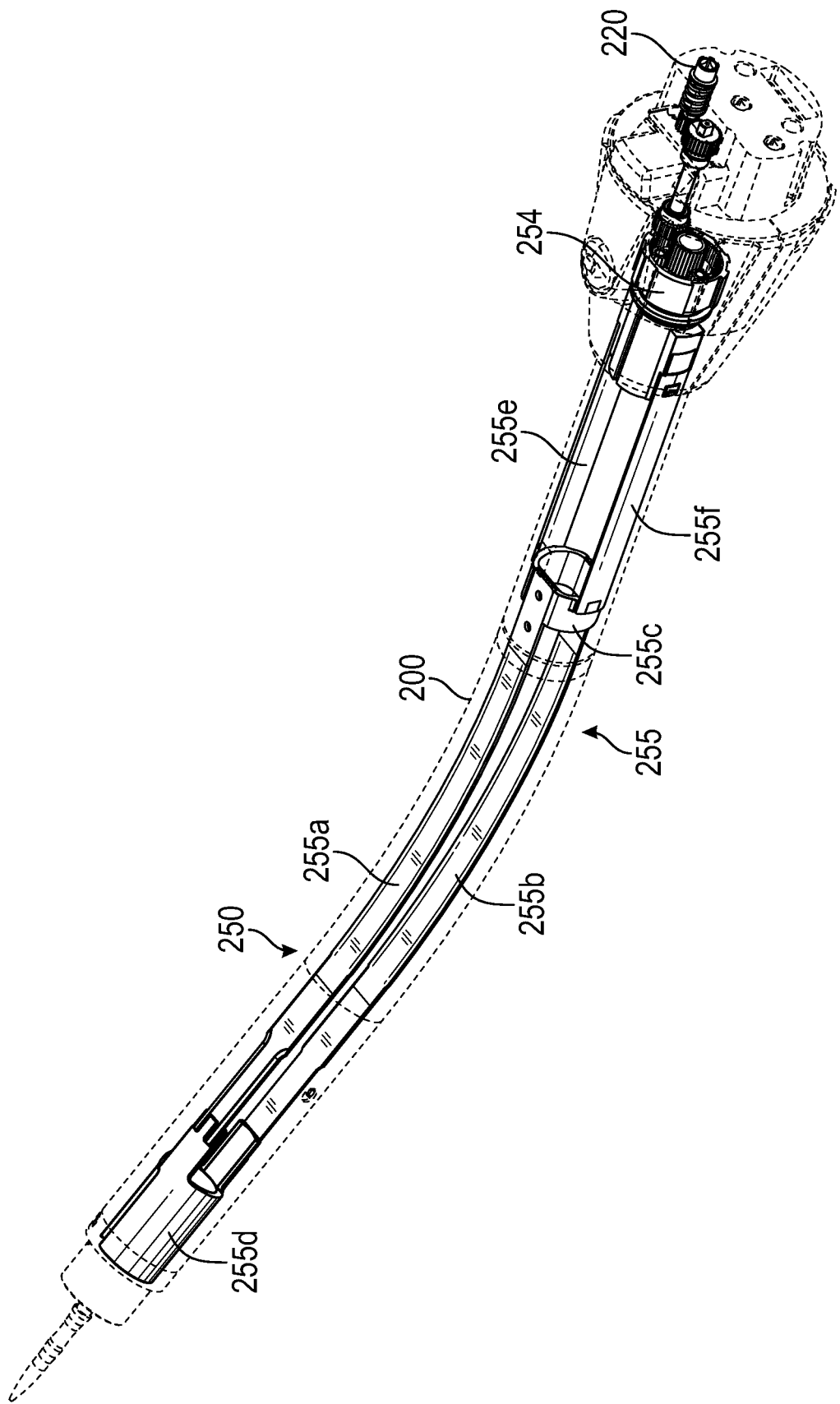
FIG. 5 is a perspective view of a stapling transmission assembly disposed within the adapter assembly of FIG. 1, shown partially in phantom.
Figure 6:
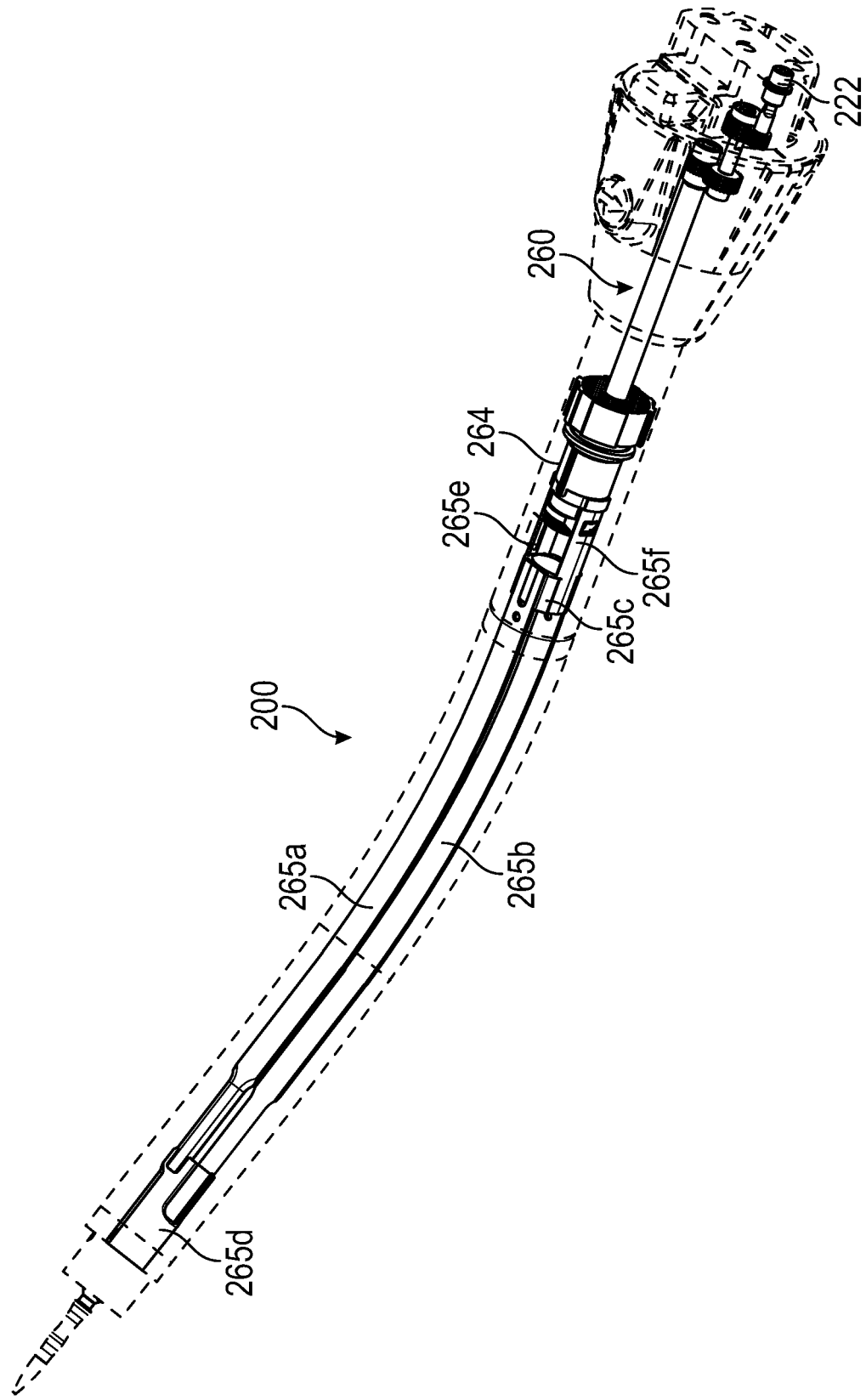
FIG. 6 is a perspective view of a cutting transmission assembly disposed within the adapter assembly of FIG. 1, shown partially in phantom.

With reference to FIG. 5, the adapter assembly 200 includes a stapling transmission assembly 250 for interconnecting the first motor 152*a* and a second axially translatable drive member of reload 400, wherein the stapling transmission assembly 250 converts and transmits a rotation of the first motor 152*a* to an axial translation of an outer flexible band assembly 255 of adapter assembly 200, and in turn, the staple driver 430 of reload 400 to fire staples 423 from the reload 400 and against anvil assembly 510.

The stapling transmission assembly 250 of adapter assembly 200 includes the outer flexible band assembly 255 secured to staple driver coupler 254. A second rotatable proximal drive shaft 220 is coupled to the second motor 152b and is configured to actuate that staple driver coupler 254, which converts rotational movement into longitudinal movement. Outer flexible band assembly 255 includes first and second flexible bands 255a, 255b laterally spaced and connected at proximal ends thereof to a support ring 255c and at distal ends thereof to a proximal end of a distal pusher 255d. Each of first and second flexible bands 255a, 255b is attached to support ring 255c and distal pusher 255d. Outer flexible band assembly 255 further includes first and second connection extensions 255e, 255f extending proximally from support ring 255c. First and second connection extensions 255e, 255f are configured to operably connect outer flexible band assembly 255 to staple driver coupler 254 of stapling transmission assembly 250.

The adapter assembly 200 also includes a cutting transmission assembly 260 for interconnecting the second motor 152b and the annular knife 444 of reload 400, wherein the cutting transmission assembly 260 converts and transmits a rotation of one of the second motor 152b to an axial translation of an outer flexible band assembly 265 of adapter assembly 200, and in turn, a knife carrier 442 of reload 400 to advance the annular knife 444 from the reload 400 and against anvil assembly 510.

Inner flexible band assembly 265 includes first and second flexible bands 265a, 265b laterally spaced and connected at proximal ends thereof to a support ring 265c and at distal ends thereof to a proximal end of a support base 265d. Each of first and second flexible bands 265a, 265b are attached to support ring 265c and support base 265d.

Inner flexible band assembly 265 further includes first and second connection extensions 265e, 265f extending proximally from support ring 265c. First and second connection extensions 265e, 265f are configured to operably connect inner flexible band assembly 265 to knife driver 264 of cutting transmission assembly 260. Support base 265d extends distally from flexible bands 265a, 265b and is configured to connect with a knife assembly 440 of reload 400.

Figure 7:
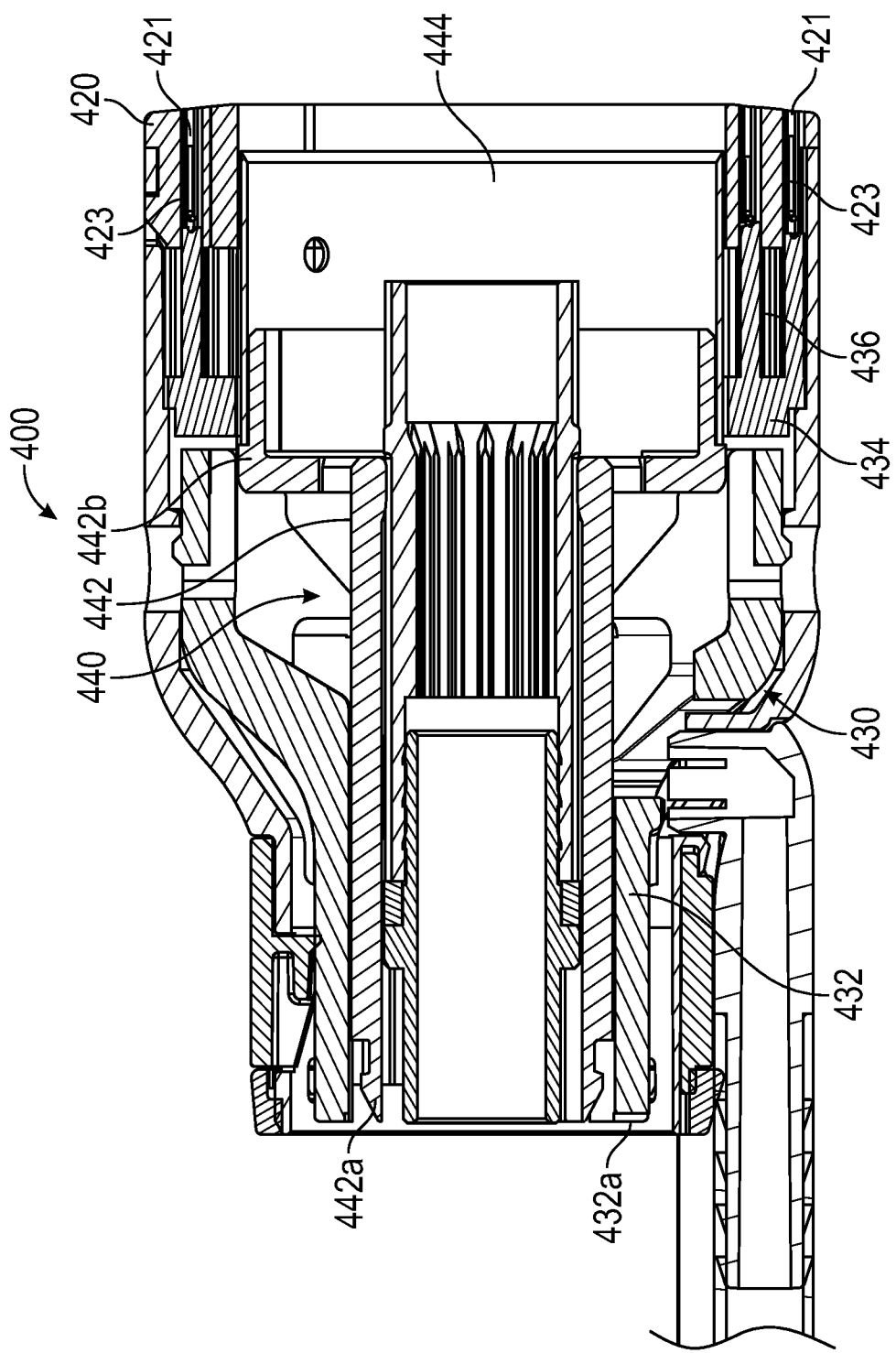
FIG. 7 is a cross-sectional view of a reload of the end effector of FIG. 1.

With reference to FIG. 7, staple driver 430 of reload 400 includes a staple cartridge 420 having a driver adapter 432 and a driver 434. A proximal end 432a of driver adapter 432 is configured for selective contact and abutment with distal pusher 255d of outer flexible band assembly 255 of stapling transmission assembly 250 of adapter assembly 200. In operation, during distal advancement of outer flexible band assembly 255, as described above, distal pusher 255d of outer flexible band assembly 255 contacts proximal end 432a of driver adapter 432 to advance driver adapter 432 and driver 434 from a first or proximal position to a second or distal position. Driver 434 includes a plurality of driver members 436 aligned with staple pockets 421 of staple cartridge 420 for contact with staples 423. Accordingly, advancement of driver 434 relative to staple cartridge 420 causes ejection of the staples 423 from staple cartridge 420.

The knife assembly 440 of the reload 400 includes a knife carrier 442 and an annular knife 444 secured about a distal end 442b of knife carrier 442. A proximal end 442a of knife carrier 442 is configured to engage the support base 265d of inner flexible band assembly. In operation, during distal advancement of inner flexible band assembly 265, support base 265d of inner flexible band assembly 265 connects with proximal end 442a of knife carrier 442 to advance knife carrier 442 and annular knife 444 from a first or proximal position to a second or advanced position to cause the cutting of tissue disposed between staple cartridge 420 and anvil assembly 510.

Forces during an actuation of trocar member 274, closing of end effector 300 (e.g., a retraction of anvil assembly 500 relative to reload 400), ejecting staples 423 from the reload 400, and advancement of the knife assembly 440 may be measured by the strain gauge 408b in order to monitor and control various processes, such as firing of staples 423 from reload 400; monitor forces during a firing and formation of the staples 423 as the staples 423 are being ejected from reload 400; optimize formation of the staples 423 (e.g., staple crimp height) as the staples 423 are being ejected from reload 400 for different indications of tissue; and monitor and control a firing of the annular knife of reload 400.

Figure 8:
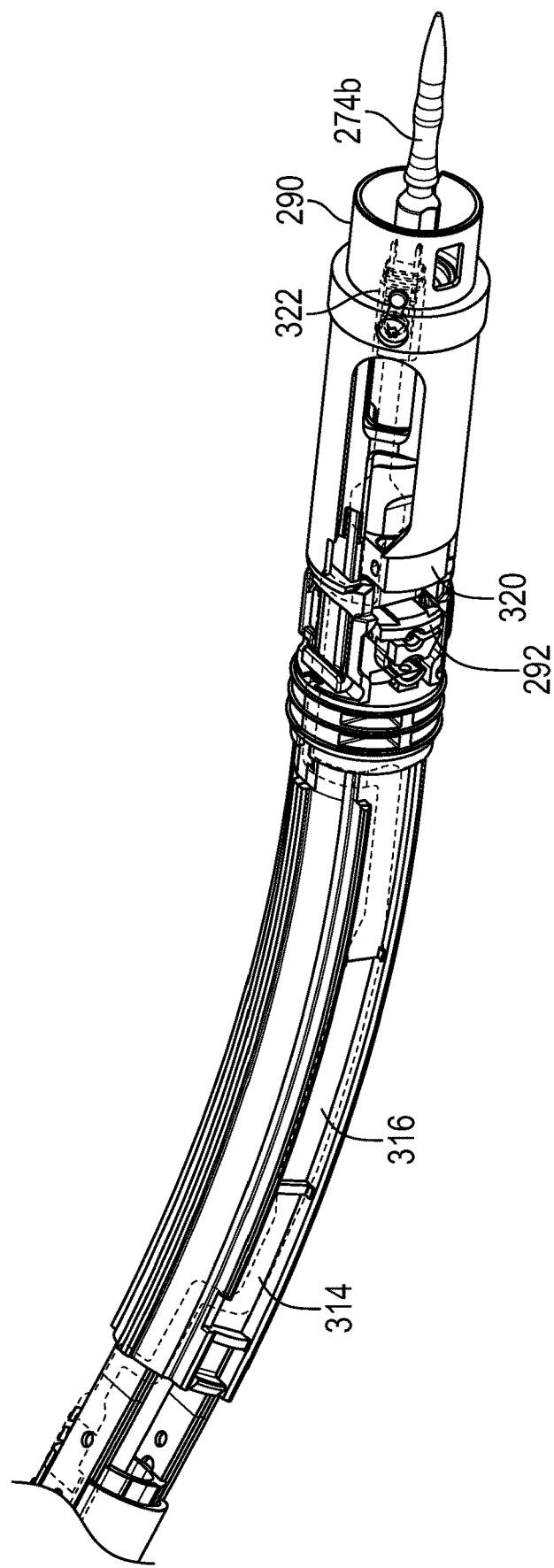
FIG. 8 is a perspective view of the adapter assembly, shown partially disassembled, with a strain gauge assembly.

With reference to FIG. 8, the strain gauge 408b of adapter assembly 200 is disposed within a strain gauge housing 320. The strain gauge 408b measures and monitors the retraction of trocar member 274 as well as the ejection and formation of the staples 423 from the reload 400. During the closing of end effector 300, when anvil assembly 500 contacts tissue, an obstruction, a tissue-contacting surface of the reload 400, staple ejection, or the like, a reaction force is exerted on anvil assembly 500 which is in a generally distal direction. This distally directed reaction force is communicated from anvil assembly 500 to the strain gauge 408b. The strain gauge 408b then communicates signals to main controller circuit board 142 of power handle 101 of handle assembly 100. Graphics (FIG. 8) are then displayed on the display 146 of handle assembly 100 to provide the user with real-time information related to the status of the firing of handle assembly 100.

The trocar assembly 270 is axially and rotationally fixed within outer tube 206 of adapter assembly 200. With reference to FIG. 8, adapter assembly 200 includes a support block 292 fixedly disposed within outer tube 206. The strain gauge housing 320 is disposed between the support block 292 and a connector sleeve 290. The reload 400 is removably coupled to the connector sleeve 290.

In operation, strain gauge 408b of adapter assembly 200 measures and monitors the retraction of trocar member 274, which passes through the strain gauge 408b. The strain gauge 408b of adapter assembly 200 also measures and monitors ejection of the staples 423 from the reload 400, since the first and second flexible bands 255a, 255b also pass through the strain gauge 408b. During clamping, stapling and cutting, a reaction force is exerted on anvil assembly 500 and the reload 400, which is communicated to support block 292, which then communicates the reaction force to a strain sensor of the strain gauge 408b.

Strain sensor of strain gauge 408b may be any device configured to measure strain (a dimensionless quantity) on an object that it is adhered to (e.g., support block 292), such that, as the object deforms, a metallic foil of the strain sensor is also deformed, causing an electrical resistance thereof to change, which change in resistance is then used to calculate loads experienced by trocar assembly 270. Strain gauge 408b provides a closed-loop feedback to a firing/clamping load exhibited by first, second and third force/rotation transmitting/converting assemblies.

Strain sensor of strain gauge 408b then communicates signals to main controller circuit board 142. Graphics are then displayed on display 146 of power-pack core assembly 106 of handle assembly 100 to provide the user with real-time information related to the status of the firing of handle assembly 100. Strain gauge 408b is also electrically connected to the electrical connector 312 (FIG. 3) via proximal and distal harness assemblies 314, 316.

For further details regarding the construction and operation of the circular stapler and its components, reference may be made to International Application Publication No. PCT/US2019/040440, filed on Jul. 3, 2019, the entire contents of which being incorporated by reference herein.

The reload 400 includes a storage device 402 and the circular adapter assembly 200 also includes a storage device 310 (FIG. 4). The storage devices 402 and 310 include non-volatile storage medium (e.g., EEPROM) that is configured to store any data pertaining to the reload 400 and the circular adapter assembly 200, respectively, including but not limited to, usage count, identification information, model number, serial number, staple size, stroke length, maximum actuation force, minimum actuation force, factory calibration data, and the like. In embodiments, the data may be encrypted and is only decryptable by devices (e.g., main controller 147) having appropriate keys. The data may also be used by the main controller 147 to authenticate the circular adapter assembly 200 and/or the reload 400. The storage devices 402 and 310 may be configured in read only or read/write modes, allowing the main controller 147 to read as well as write data onto the storage device 402 and 310.

Prior to operation of the powered circular stapler 10, the power handle 101 is enclosed within the shell housing 11 the adapter assembly 200 is coupled to handle assembly 100. After attachment of circular adapter assembly 200, handle assembly 100 initially verifies that circular adapter assembly 200 is coupled thereto by establishing communications with the storage device 310 of the circular adapter assembly 200 and authenticates circular adapter assembly 200. The data (e.g., usage count) stored on the storage device 310 is encrypted and is authenticated by the power handle 101 prior to determining whether the usage count stored on the storage device 310 exceeds the threshold (e.g., if the adapter assembly 200 has been previously used). Power handle 101 then performs verification checks (e.g., end of life checks, trocar member 274 missing, etc.) and calibrates circular adapter assembly 200 after the handle assembly 100 confirms that the trocar member 274 is attached.

Figure 9:
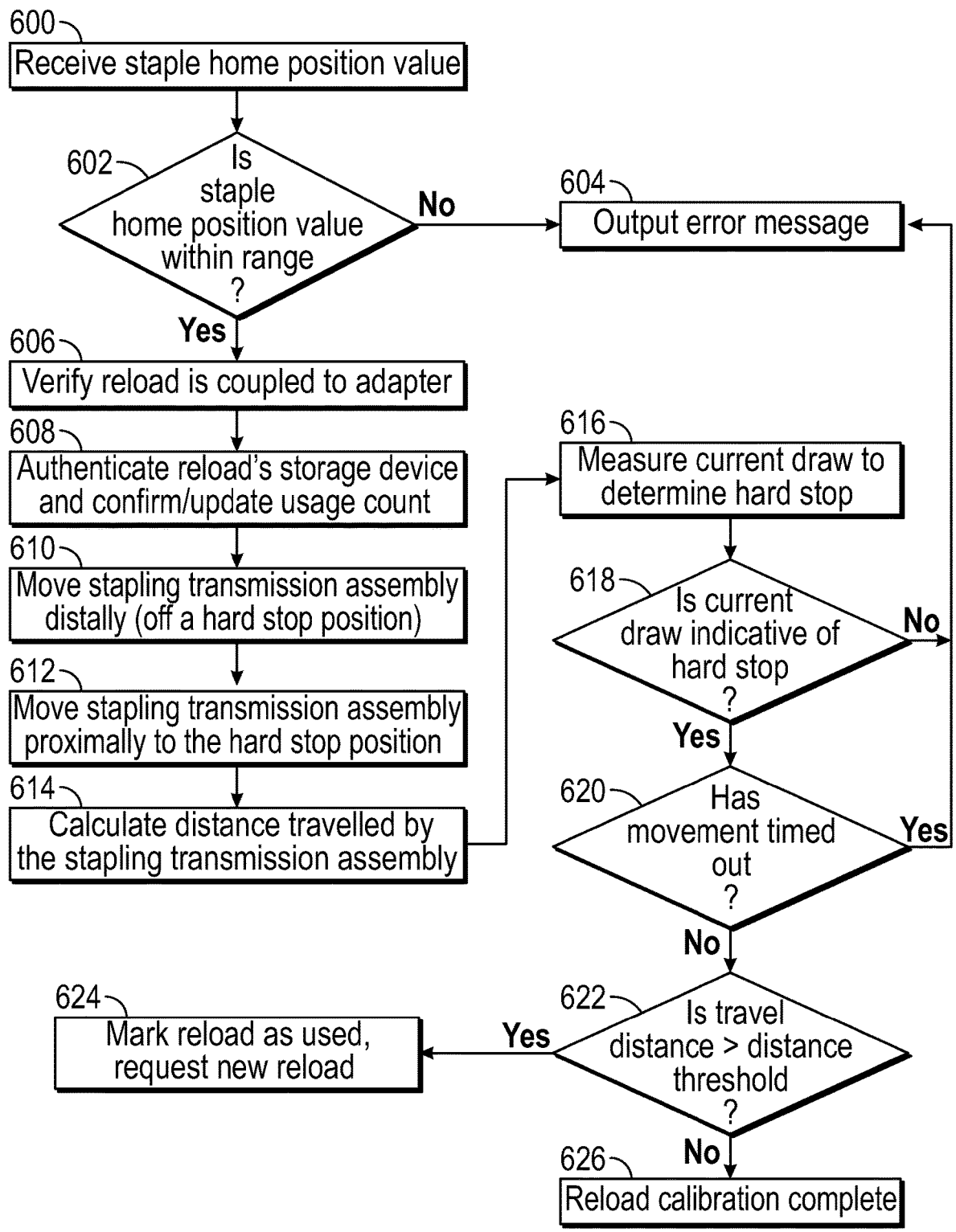
FIG. 9 is a flow chart of a method for controlling the powered circular stapler during a stapling calibration process according to an embodiment of the present disclosure.

With reference to FIG. 9 a method for determining whether the staples 423 of the reload 400 have been previously ejected includes, at step 600, the main controller 147 receiving a staple home position value, e.g., by reading from the storage device 310, and calculating other staple position reference values, such as calibration position. At step 602, the main controller 147 also compares the staple home position value read from the storage device 310 to the maximum and minimum values stored in the memory 141. If the value is outside the range, at step 604, an error screen is displayed and the power handle 101 transitions to a lock up state, preventing use of the adapter assembly 200. The absolute minimum value is set at 0.0 turns for the first motor 152a.

If the staple home position value is within the expected absolute values, the adapter assembly 200 may be used and the reload 400 is coupled to circular adapter assembly 200. At step 606, the handle assembly 100 verifies that reload 400 is attached to circular adapter assembly 200 by establishing communications with the storage device 402 of reload 400.

At step 608, the power handle 101 authenticates the storage device 402 and confirms that circular reload 400 has not been previously fired by checking the usage count. The usage count is adjusted and encoded by handle assembly 100 after use of reload 400. If circular reload 400 has been previously used, handle assembly 100 displays an error indicating the same on the display screen 146.

Figure 10:
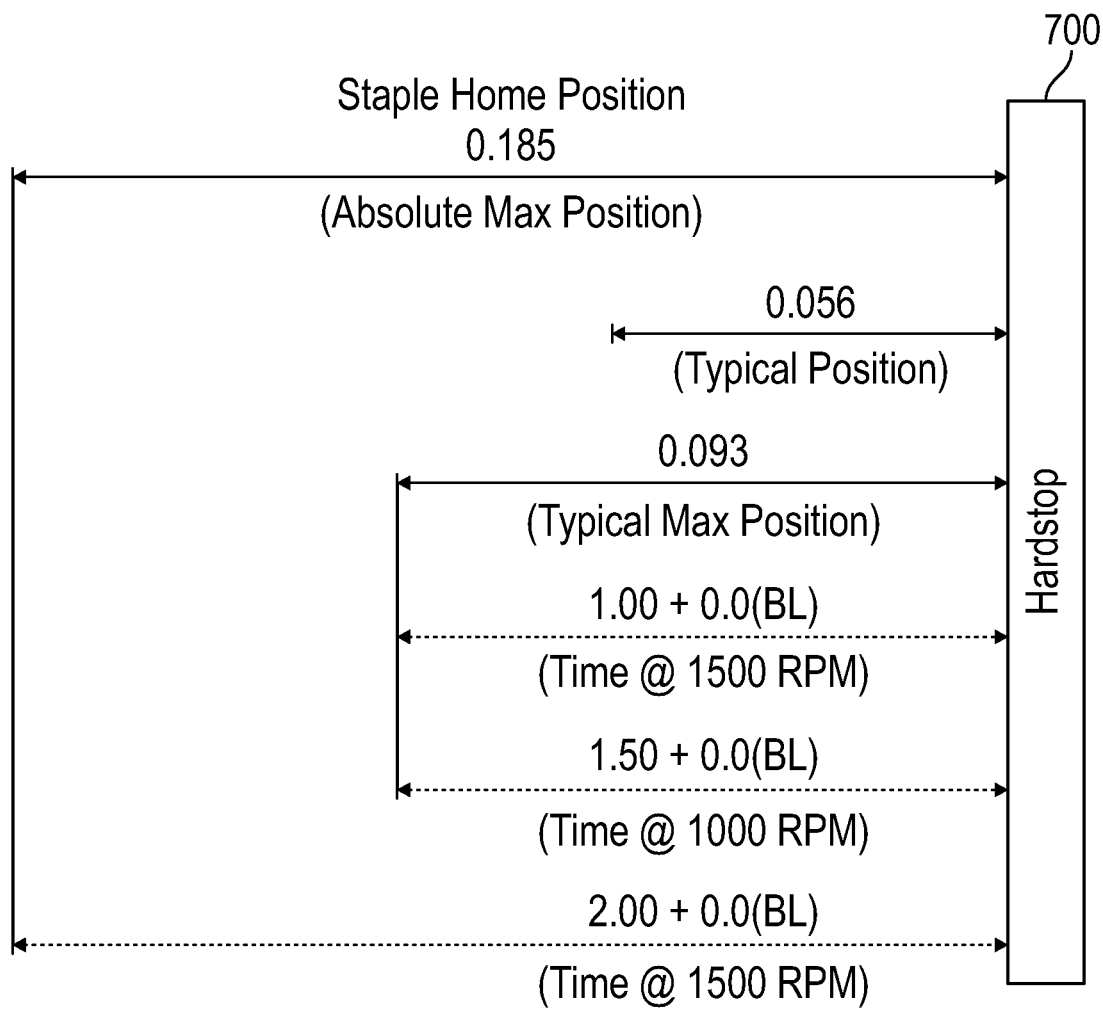
FIG. 10 is a schematic diagram illustrating travel distance of a stapling transmission assembly and corresponding motor rotational speed during the stapling calibration process according to an embodiment of the present disclosure.

At step 610, the power handle 101 performs a staple calibration process including moving stapling transmission assembly 250 distally for a short period of time (e.g., about 200 milliseconds) to move the stapling transmission assembly 250 off a hard stop position 700 (FIG. 10), which is a proximal mechanical limit. This is done for the purpose of moving the stapling transmission assembly 250 off the hard stop position 700 in the event that the stapling transmission assembly 250 is already pinned against the hard stop position 700.

At step 612, the stapling transmission assembly 250 is moved proximally by the first motor 152a to the hard stop position 700 to establish a zero-position reference point. The stapling transmission assembly 250 may be disposed at any distance away from the hard stop position 700. However, if the distance is too large, then the stapling transmission assembly 250 may inadvertently push out the staples 423 of the reload 400. The following steps determine whether the staples 423 have been previously ejected, by checking the distance travelled by the stapling transmission assembly 250 to the hard stop position 700.

At step 614, the main controller 147 calculates the distance travelled by the stapling transmission assembly 250, i.e., by monitoring rotations of the first motor 152a. The first motor 152a moves the stapling transmission assembly 250 until a specified current limit is detected indicative of the stapling transmission assembly 250 hitting the hard stop position 700.

At step 616, the main controller 147 also monitors the current draw of the movement. At step 618, the main controller 147 compares the measured current draw to a current limit, and if the current limit is exceeded before reaching the hard stop position 700 due to a mechanical malfunction, e.g., broken gears, motor, etc., the main controller 147 exits calibration and outputs an error message at step 604 and/or requests a new adapter assembly 200 and/or handle assembly 100.

The main controller 147 also monitors the time during the movement, and if the motor movement times-out (e.g., 5-20 seconds), due to a mechanical malfunction, e.g., broken gears, motor, etc. At step 620, the main controller 147 continuously checks if a time out has occurred, and if the time limit is exceeded before the hard stop is reached, the main controller 147 exits calibration and outputs an error message at step 604 and/or requests a new adapter assembly 200 and/or handle assembly 100.

At step 622, the main controller 147 utilizes the traveled distance during calibration to confirm that the reload 400 is unused. Thus, if the traveled distance is determined to be above a predetermined hard stop threshold, then the main controller 147 confirms that the staples 423 were previously ejected from the reload 400 and at step 624 marks the reload 400 as used, regardless of the previous status of the reload 400. The main controller 147 exits calibration and may output an error message and/or requests a new reload 400.

At step 626, the calibration is successfully completed once the hard stop position 700 is reached within the predetermined time, without exceeding time, current, and distance thresholds.

It will be understood that various modifications may be made to the embodiments of the presently disclosed circular staplers. Therefore, the above description should not be construed as limiting, but merely as exemplifications of embodiments. Those skilled in the art will envision other modifications within the scope and spirit of the present disclosure.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

What is claimed is:

1. A surgical device comprising:
   a power source;
   a motor coupled to the power source;
   a transmission assembly movable by the motor;
   a reload, carrying staples, coupled to the transmission assembly; and
   a controller configured to perform a stapling operation calibration process when the reload is connected and prior to an intended firing of the staples, during which the controller is configured to:
      operate, as part of first portion of the calibration process, the motor to move the transmission assembly distally from a proximal position to a distal position;
      subsequent to operating the motor to move the transmission assembly distally, operate, as a second portion of the calibration process, the motor to move the transmission assembly proximally from the distal position until a hard stop is reached;
      determine a distance traveled by the transmission assembly during movement from the distal position to the hard stop; and
      compare the traveled distance with a threshold distance to determine whether the distal movement of the transmission assembly during the first portion of the calibration process caused one or more of the staples to be prematurely ejected as part of the calibration process.

2. The surgical device according to claim 1, wherein the reload includes a storage device.

3. The surgical device according to claim 2, wherein the controller is further configured to update a status of the reload stored on the storage device in response to a determination that one or more of the staples were prematurely ejected.

4. The surgical device according to claim 1, wherein the distance travelled by the transmission assembly is greater than the threshold distance, and the determination indicates one or more staples were prematurely ejected.

5. The surgical device according to claim 1, wherein the controller is further configured to determine that the reload is empty of the staples based on the distance travelled by the transmission assembly to reach the hard stop exceeding the threshold distance.

6. The surgical device according to claim 1, further comprising a current sensor configured to measure a current draw of the motor.

7. The surgical device according to claim 6, wherein the controller is further configured to determine that the transmission assembly has reached the hard stop based on the current draw of the motor.

8. A surgical device comprising:
   an adapter assembly including:
      a transmission assembly;
      a reload coupled to the transmission assembly;
   a handle assembly including:
      a power source; and
      a motor coupled to the power source, the motor configured to move the transmission assembly; and
   a controller configured to perform a stapling operation calibration process, during which the controller is configured to:
      operate, during a first portion of the calibration process, the motor to move the transmission assembly distally from an initial position to a distal position;
      operate, during a second portion of the calibration process, the motor to move the transmission assembly proximally from the distal position until a hard stop is reached, wherein the hard stop is positioned proximally from the initial position;
      determine a distance traveled by the transmission assembly during movement from the distal position to the hard stop based on revolutions of the motor; and
      compare the determined distance traveled to a threshold distance to determine that one or more of the staples have been ejected.

9. The surgical device according to claim 8, wherein the reload includes a storage device.

10. The surgical device according to claim 9, wherein the controller is further configured to update a status of the reload stored on the storage device in response to determining that the one or staples were prematurely ejected.

11. The surgical device according to claim 8, wherein the distance travelled by the transmission assembly to reach the hard stop exceeds the threshold distance.

12. The surgical device according to claim 8, further comprising a current sensor configured to measure a current draw of the motor.

13. The surgical device according to claim 12, wherein the controller is further configured to determine the transmission assembly reaching the hard stop based on the current draw of the motor.

14. A method for operating a powered surgical device, the method comprising:
   performing a stapling operation calibration process including:
      operating, as a first portion of the calibration process, a motor to move a transmission assembly distally from an initial position to a distal position, wherein a reload comprising staples is coupled to the transmission assembly;
      operating, as a second portion of the calibration process, the motor to move the transmission assembly proximally from the distal position until a hard stop is reached;
      determining a distance travelled by the transmission assembly during movement from the distal position to the hard stop; and
      comparing the determined distance travelled to a threshold distance to whether the distal movement of the transmission assembly to determine that one or more the staples have been prematurely ejected from the reload as part of the first portion of the calibration process.

15. The method according to claim 14, further comprising:
updating a status of the reload stored on a storage device in response to determining that the one or more staples have been prematurely ejected.

16. The method according to claim 14, wherein the distance travelled by the transmission assembly exceeds the threshold distance.

17. The method according to claim 14, further comprising:
determining that the transmission assembly reached the hard stop based on a current draw of the motor.

* * * * *